(12) United States Patent
Mudumba et al.

(10) Patent No.: US 8,637,070 B2
(45) Date of Patent: *Jan. 28, 2014

(54) RAPAMYCIN FORMULATIONS AND METHODS OF THEIR USE

(75) Inventors: Sreenivasu Mudumba, Union City, CA (US); Philippe J M Dor, Cupertino, CA (US); Thierry Nivaggioli, Atherton, CA (US); David A. Weber, Danville, CA (US); Sidiq Farooq, Newark, CA (US)

(73) Assignee: Santen Pharmaceutical Co., Ltd., Osaka (JP)

( * ) Notice: Subject to any disclaimer, the term of this patent is extended or adjusted under 35 U.S.C. 154(b) by 1197 days.

This patent is subject to a terminal disclaimer.

(21) Appl. No.: 11/352,092

(22) Filed: Feb. 9, 2006

(65) Prior Publication Data

US 2006/0264453 A1 Nov. 23, 2006

Related U.S. Application Data

(60) Provisional application No. 60/664,306, filed on Mar. 21, 2005, provisional application No. 60/664,040, filed on Mar. 21, 2005, provisional application No. 60/651,790, filed on Feb. 9, 2005.

(51) Int. Cl.
*A61K 9/00* (2006.01)
*A61F 2/00* (2006.01)

(52) U.S. Cl.
USPC ............................. 424/427; 424/400; 514/912

(58) Field of Classification Search
None
See application file for complete search history.

(56) References Cited

U.S. PATENT DOCUMENTS

| | | |
|---|---|---|
| 3,416,530 A | 12/1968 | Ness |
| 3,630,200 A | 12/1971 | Higuchi |
| 3,828,777 A | 8/1974 | Ness |
| 3,914,402 A | 10/1975 | Shell |
| 3,926,188 A | 12/1975 | Baker et al. |
| 4,014,335 A | 3/1977 | Arnold |
| 4,093,709 A | 6/1978 | Choi et al. |
| 4,300,557 A | 11/1981 | Refojo et al. |
| 4,316,885 A | 2/1982 | Rakhit |
| 4,650,803 A | 3/1987 | Stella et al. |
| 4,853,224 A | 8/1989 | Wong |
| 4,946,450 A | 8/1990 | Erwin |
| 4,997,652 A | 3/1991 | Wong |
| 5,011,844 A | 4/1991 | Fehr |
| 5,023,262 A | 6/1991 | Caufield et al. |
| 5,078,999 A | 1/1992 | Warner et al. |
| 5,100,899 A | 3/1992 | Calne |
| 5,120,725 A | 6/1992 | Kao et al. |
| 5,120,727 A | 6/1992 | Kao et al. |
| 5,120,842 A | 6/1992 | Failli et al. |
| 5,147,647 A | 9/1992 | Darougar |
| 5,164,188 A | 11/1992 | Wong |
| 5,177,203 A | 1/1993 | Failli et al. |
| 5,178,635 A | 1/1993 | Gwon et al. |
| 5,189,042 A | 2/1993 | Goulet et al. |
| 5,192,773 A | 3/1993 | Armistead et al. |
| 5,192,802 A | 3/1993 | Rencher |
| 5,258,389 A | 11/1993 | Goulet et al. |
| 5,300,114 A | 4/1994 | Gwon et al. |
| 5,322,691 A | 6/1994 | Darougar et al. |
| 5,368,865 A | 11/1994 | Asakura et al. |
| 5,378,475 A | 1/1995 | Smith et al. |
| 5,387,589 A | 2/1995 | Kulkarni |
| 5,395,618 A | 3/1995 | Darougar et al. |
| 5,403,901 A | 4/1995 | Namdaran et al. |
| 5,443,505 A | 8/1995 | Wong et al. |
| 5,457,111 A | 10/1995 | Luly et al. |
| 5,466,233 A | 11/1995 | Weiner et al. |
| 5,514,686 A | 5/1996 | Mochizuki et al. |
| 5,516,522 A | 5/1996 | Peyman et al. |
| 5,516,770 A | 5/1996 | Waranis et al. |
| 5,516,781 A | 5/1996 | Morris et al. |
| 5,527,907 A | 6/1996 | Or et al. |
| 5,530,006 A | 6/1996 | Waranis et al. |
| 5,532,248 A | 7/1996 | Goulet et al. |
| 5,536,729 A | 7/1996 | Waranis et al. |
| 5,559,121 A | 9/1996 | Harrison et al. |
| 5,583,139 A | 12/1996 | Or et al. |
| 5,601,844 A | 2/1997 | Kagayama et al. |
| 5,614,547 A | 3/1997 | Hamilton et al. |
| 5,616,588 A | 4/1997 | Waranis et al. |
| 5,621,108 A | 4/1997 | Smith, III et al. |
| 5,632,984 A | 5/1997 | Wong et al. |
| 5,672,605 A | 9/1997 | Or et al. |

(Continued)

FOREIGN PATENT DOCUMENTS

| | | |
|---|---|---|
| CN | 1333018 A | 1/2002 |
| CN | 1340358 A | 3/2002 |

(Continued)

OTHER PUBLICATIONS

Thomas A. Ciulla, et al, Age-Related Macular Degeneration: A Review of Experimental Treatments, 43 Surv. Ophthalmol. 134, 136-38 (Sep.-Oct. 1998.*

(Continued)

*Primary Examiner* — Brian-Yong Kwon
*Assistant Examiner* — Mark V Stevens
(74) *Attorney, Agent, or Firm* — Morrison & Foerster LLP

(57) ABSTRACT

Described herein are liquid rapamycin formulations. Described herein are methods of treating or preventing diseases or conditions, such as choroidal neovascularization, wet AMD and dry AMD, and preventing transition of dry AMD to wet AMD, using the liquid rapamycin formulations described herein.

8 Claims, 5 Drawing Sheets

(56) References Cited

U.S. PATENT DOCUMENTS

| | | |
|---|---|---|
| 5,679,666 A | 10/1997 | Clark |
| 5,696,135 A | 12/1997 | Steiner et al. |
| 5,725,493 A | 3/1998 | Avery et al. |
| 5,743,274 A | 4/1998 | Peyman |
| 5,766,242 A | 6/1998 | Wong et al. |
| 5,766,619 A | 6/1998 | Aiache et al. |
| 5,770,592 A | 6/1998 | Clark |
| 5,773,019 A | 6/1998 | Ashton et al. |
| 5,773,021 A | 6/1998 | Gurtler et al. |
| 5,798,355 A | 8/1998 | Steiner et al. |
| 5,800,807 A | 9/1998 | Hu et al. |
| 5,824,072 A | 10/1998 | Wong |
| 5,830,173 A | 11/1998 | Avery et al. |
| 5,883,082 A | 3/1999 | Bennett et al. |
| 5,902,598 A | 5/1999 | Chen et al. |
| 5,904,144 A | 5/1999 | Hammang et al. |
| 5,912,253 A | 6/1999 | Cottens et al. |
| 6,004,973 A | 12/1999 | Guitard et al. |
| 6,007,510 A | 12/1999 | Nigam |
| 6,015,815 A | 1/2000 | Mollison |
| 6,034,239 A | 3/2000 | Ohkawa et al. |
| 6,074,661 A | 6/2000 | Olejnik et al. |
| 6,110,485 A | 8/2000 | Olejnik et al. |
| 6,126,687 A | 10/2000 | Peyman |
| 6,142,969 A | 11/2000 | Nigam |
| 6,217,895 B1 | 4/2001 | Guo et al. |
| 6,239,102 B1 | 5/2001 | Tiemessen |
| 6,239,113 B1 | 5/2001 | Dawson et al. |
| 6,254,860 B1 | 7/2001 | Garst |
| 6,258,856 B1 | 7/2001 | Chamberlain et al. |
| 6,267,985 B1 | 7/2001 | Chen et al. |
| 6,306,422 B1 | 10/2001 | Batich et al. |
| 6,326,387 B1 | 12/2001 | Armistead |
| 6,329,386 B1 | 12/2001 | Mollison |
| 6,331,313 B1 | 12/2001 | Wong et al. |
| 6,350,442 B2 | 2/2002 | Garst |
| 6,361,760 B1 | 3/2002 | Murata et al. |
| 6,375,972 B1 | 4/2002 | Guo et al. |
| 6,376,517 B1 | 4/2002 | Ross et al. |
| 6,378,526 B1 | 4/2002 | Bowman et al. |
| 6,387,918 B1 | 5/2002 | Yamanaka et al. |
| 6,397,849 B1 | 6/2002 | Bowman et al. |
| 6,399,629 B1 | 6/2002 | Chamberland et al. |
| 6,413,245 B1 | 7/2002 | Yaacobi et al. |
| 6,413,540 B1 | 7/2002 | Yaacobi |
| 6,416,777 B1 | 7/2002 | Yaacobi |
| 6,440,990 B1 | 8/2002 | Cottens et al. |
| 6,455,518 B2 | 9/2002 | Zenke et al. |
| 6,482,802 B1 | 11/2002 | Hu et al. |
| 6,489,335 B2 | 12/2002 | Peyman |
| 6,534,693 B2 | 3/2003 | Fischell et al. |
| 6,576,224 B1 | 6/2003 | Osbakken et al. |
| 6,617,345 B1 | 9/2003 | Gregory et al. |
| 6,632,836 B1 | 10/2003 | Baker et al. |
| 6,656,460 B2 | 12/2003 | Benita et al. |
| 6,699,493 B2 | 3/2004 | Wong |
| 6,713,081 B2 | 3/2004 | Robinson et al. |
| 6,719,750 B2 | 4/2004 | Varner et al. |
| 6,777,000 B2 | 8/2004 | Ni et al. |
| 6,787,179 B2 | 9/2004 | Timm et al. |
| 6,812,220 B2 | 11/2004 | Jackson et al. |
| 6,864,232 B1 | 3/2005 | Ueno |
| 6,872,383 B2 | 3/2005 | Ueno |
| 6,890,546 B2 | 5/2005 | Mollison et al. |
| 6,939,878 B2 | 9/2005 | Naicker et al. |
| 6,956,043 B2 | 10/2005 | Guitard et al. |
| 7,014,861 B2 | 3/2006 | Roorda et al. |
| 7,018,808 B2 | 3/2006 | Leadlay et al. |
| 7,033,604 B2 | 4/2006 | Ueno |
| 7,033,605 B2 | 4/2006 | Wong |
| 7,034,037 B2 | 4/2006 | Arnold et al. |
| 7,063,857 B1 | 6/2006 | Ueno |
| 7,083,802 B2 | 8/2006 | Peyman |
| 7,083,803 B2 | 8/2006 | Peyman |
| 7,087,237 B2 | 8/2006 | Peyman |
| 7,128,897 B2 | 10/2006 | Osbakken et al. |
| 7,160,867 B2 | 1/2007 | Abel et al. |
| 7,181,287 B2 | 2/2007 | Greenberg |
| 7,183,289 B2 | 2/2007 | Zhang et al. |
| 7,186,518 B2 | 3/2007 | Wang et al. |
| 7,223,286 B2 | 5/2007 | Wright et al. |
| 7,354,574 B2 | 4/2008 | Peyman |
| 7,402,399 B2 | 7/2008 | Mukherjeei et al. |
| 6,376,517 C1 | 3/2009 | Ross et al. |
| 8,367,097 B2 | 2/2013 | Mudumba et al. |
| 2002/0187998 A1 | 12/2002 | Ueno |
| 2003/0018044 A1 | 1/2003 | Peyman |
| 2003/0027744 A1 | 2/2003 | Dana et al. |
| 2003/0069232 A1 | 4/2003 | Chiou |
| 2003/0069560 A1 | 4/2003 | Adamis et al. |
| 2003/0077297 A1 | 4/2003 | Chen et al. |
| 2003/0171320 A1 | 9/2003 | Guyer |
| 2003/0190286 A1 | 10/2003 | Dugger, III |
| 2003/0203892 A1* | 10/2003 | Keller et al. .............. 514/211.09 |
| 2003/0236310 A1* | 12/2003 | Nathan et al. .............. 514/772.4 |
| 2004/0018228 A1 | 1/2004 | Fischell et al. |
| 2004/0022755 A1 | 2/2004 | Kamath |
| 2004/0057958 A1 | 3/2004 | Waggoner, Jr. et al. |
| 2004/0167152 A1 | 8/2004 | Rubino et al. |
| 2004/0175428 A1 | 9/2004 | Appel et al. |
| 2004/0180075 A1 | 9/2004 | Robinson et al. |
| 2004/0198763 A1 | 10/2004 | Ueno |
| 2004/0219181 A1 | 11/2004 | Viscasillas |
| 2004/0224394 A1 | 11/2004 | Katz et al. |
| 2004/0234611 A1 | 11/2004 | Ahlheim et al. |
| 2005/0031650 A1 | 2/2005 | Leroux et al. |
| 2005/0032826 A1 | 2/2005 | Mollison et al. |
| 2005/0042215 A1 | 2/2005 | Owen et al. |
| 2005/0048123 A1 | 3/2005 | Su et al. |
| 2005/0064010 A1 | 3/2005 | Cooper et al. |
| 2005/0074497 A1 | 4/2005 | Schultz |
| 2005/0084514 A1 | 4/2005 | Shebuski et al. |
| 2005/0123605 A1 | 6/2005 | Hunter et al. |
| 2005/0142162 A1 | 6/2005 | Hunter et al. |
| 2005/0143363 A1 | 6/2005 | De Juan et al. |
| 2005/0187241 A1* | 8/2005 | Wen et al. .................... 514/291 |
| 2005/0196440 A1 | 9/2005 | Masters et al. |
| 2005/0222191 A1 | 10/2005 | Falotico et al. |
| 2005/0232952 A1 | 10/2005 | Lambert et al. |
| 2005/0232965 A1 | 10/2005 | Falotico |
| 2005/0249710 A1 | 11/2005 | Wong |
| 2005/0250804 A1 | 11/2005 | Kannan et al. |
| 2005/0255144 A1 | 11/2005 | Schultz |
| 2006/0002971 A1 | 1/2006 | Saltzman et al. |
| 2006/0024350 A1 | 2/2006 | Varner et al. |
| 2006/0034891 A1 | 2/2006 | Lawin et al. |
| 2006/0073182 A1 | 4/2006 | Wong et al. |
| 2006/0121115 A1 | 6/2006 | Leroux et al. |
| 2006/0141049 A1 | 6/2006 | Lyons et al. |
| 2006/0182771 A1 | 8/2006 | Dor et al. |
| 2006/0182783 A1 | 8/2006 | Hughes et al. |
| 2006/0198867 A1 | 9/2006 | Toner et al. |
| 2006/0216288 A1 | 9/2006 | Chang |
| 2006/0228393 A1 | 10/2006 | Peyman |
| 2006/0228394 A1 | 10/2006 | Peyman |
| 2006/0247265 A1 | 11/2006 | Clackson et al. |
| 2006/0257450 A1 | 11/2006 | Mudumba et al. |
| 2006/0258698 A1 | 11/2006 | Mudumba et al. |
| 2006/0263409 A1 | 11/2006 | Peyman |
| 2006/0275218 A1 | 12/2006 | Tamarkin et al. |
| 2007/0014760 A1 | 1/2007 | Peyman |
| 2007/0015697 A1 | 1/2007 | Peyman |
| 2007/0173538 A1 | 7/2007 | Han et al. |
| 2007/0203173 A1 | 8/2007 | Mudumba et al. |
| 2007/0265294 A1 | 11/2007 | Kleinman et al. |
| 2009/0036479 A1 | 2/2009 | Wen et al. |
| 2009/0074786 A1 | 3/2009 | Dor et al. |
| 2009/0324686 A1 | 12/2009 | Cooper et al. |
| 2009/0324687 A1 | 12/2009 | Cooper et al. |
| 2009/0324688 A1 | 12/2009 | Cooper et al. |
| 2009/0324689 A1 | 12/2009 | Cooper et al. |
| 2009/0324690 A1 | 12/2009 | Cooper et al. |
| 2010/0227879 A1 | 9/2010 | Mudumba et al. |
| 2012/0034279 A1 | 2/2012 | Cooper et al. |

(56) References Cited

U.S. PATENT DOCUMENTS

FOREIGN PATENT DOCUMENTS

| | | |
|---|---|---|
| CN | 1456350 A | 11/2003 |
| DE | 40225553 A1 | 1/1992 |
| DE | 19810655 A1 | 9/1999 |
| EP | 0041745 A1 | 12/1981 |
| EP | 0041795 A2 | 12/1981 |
| EP | 0467606 A1 | 1/1992 |
| EP | 0650730 A1 | 5/1995 |
| EP | 0904787 A1 | 3/1999 |
| EP | 1142566 A1 | 10/2001 |
| EP | 1126849 B1 | 3/2005 |
| FR | 2382240 C1 | 9/1978 |
| GB | 2278780 A | 12/1994 |
| JP | 09-030966 | 2/1997 |
| JP | 09-315954 | 12/1997 |
| JP | 10-218787 | 8/1998 |
| JP | 2001-064198 | 3/2001 |
| JP | 2002-522485 A | 7/2002 |
| JP | 2002-534139 A | 10/2002 |
| JP | 2002-332225 | 11/2002 |
| RU | 2123314 C1 | 12/1998 |
| RU | 2149615 C1 | 5/2000 |
| WO | WO-89/01772 A1 | 3/1989 |
| WO | WO-92/05179 A1 | 4/1992 |
| WO | WO-93/19763 A1 | 10/1993 |
| WO | WO-94/05257 A1 | 3/1994 |
| WO | WO-94/21642 A1 | 9/1994 |
| WO | WO-95/14023 A1 | 5/1995 |
| WO | WO-95/26734 A1 | 10/1995 |
| WO | WO-95/28984 A1 | 11/1995 |
| WO | WO-96/36377 A1 | 11/1996 |
| WO | WO-96/40140 A1 | 12/1996 |
| WO | WO-96/41865 A1 | 12/1996 |
| WO | WO-97/10806 A1 | 3/1997 |
| WO | WO-97/16068 A1 | 5/1997 |
| WO | WO-99/07418 A2 | 2/1999 |
| WO | WO-99/11244 A1 | 3/1999 |
| WO | WO-99/20261 A2 | 4/1999 |
| WO | WO-99/22722 A2 | 5/1999 |
| WO | WO-99/34830 A1 | 7/1999 |
| WO | WO-99/37667 A1 | 7/1999 |
| WO | WO-99/45920 A2 | 9/1999 |
| WO | WO-99/58126 A1 | 11/1999 |
| WO | 00/09109 A2 | 2/2000 |
| WO | WO-00/06121 A1 | 2/2000 |
| WO | WO-00/09109 A2 | 2/2000 |
| WO | WO-00/09109 A3 | 2/2000 |
| WO | WO-00/09112 A2 | 2/2000 |
| WO | WO-00/09479 A2 | 2/2000 |
| WO | WO-00/28945 A2 | 5/2000 |
| WO | WO-00/33878 A2 | 6/2000 |
| WO | WO-00/37066 A2 | 6/2000 |
| WO | 00/40089 A1 | 7/2000 |
| WO | WO-00/38703 A1 | 7/2000 |
| WO | WO-00/40089 A1 | 7/2000 |
| WO | WO-00/56340 A1 | 9/2000 |
| WO | WO-00/66122 A1 | 11/2000 |
| WO | WO-01/28522 A2 | 4/2001 |
| WO | WO-01/30386 A1 | 5/2001 |
| WO | WO-01/42219 A2 | 6/2001 |
| WO | WO-01/47495 A1 | 7/2001 |
| WO | 01/60345 A2 | 8/2001 |
| WO | WO-01/93830 A1 | 12/2001 |
| WO | WO-02/28387 A1 | 4/2002 |
| WO | WO-02/062335 A2 | 8/2002 |
| WO | WO-02/066019 A2 | 8/2002 |
| WO | WO-02/074196 A1 | 9/2002 |
| WO | WO-02/100318 A2 | 12/2002 |
| WO | 03/007944 A1 | 1/2003 |
| WO | WO-03/017990 A2 | 3/2003 |
| WO | WO-03/051385 A1 | 6/2003 |
| WO | WO-03/068186 A1 | 8/2003 |
| WO | 03/075885 A1 | 9/2003 |
| WO | WO-03/074027 A2 | 9/2003 |
| WO | WO-03/074029 A1 | 9/2003 |
| WO | 03/092671 A1 | 11/2003 |
| WO | 03/097009 A1 | 11/2003 |
| WO | WO-03/090684 A2 | 11/2003 |
| WO | WO-2004/007709 A2 | 1/2004 |
| WO | WO-2004/011000 A1 | 2/2004 |
| WO | WO-2004/014373 A1 | 2/2004 |
| WO | WO-2004/019904 A1 | 3/2004 |
| WO | WO-2004/027027 A2 | 4/2004 |
| WO | WO-2004/027027 A3 | 4/2004 |
| WO | WO-2004/028477 A2 | 4/2004 |
| WO | WO-2004/043480 A2 | 5/2004 |
| WO | WO-2004/060283 A2 | 7/2004 |
| WO | WO-2004/074445 A2 | 9/2004 |
| WO | WO-2004/096261 A1 | 11/2004 |
| WO | WO-2005/002625 A2 | 1/2005 |
| WO | WO-2005/011813 A2 | 2/2005 |
| WO | WO-2005/020962 A1 | 3/2005 |
| WO | WO-2005/027906 | 3/2005 |
| WO | WO-2005/030205 A1 | 4/2005 |
| WO | 2005/044259 A1 | 5/2005 |
| WO | WO-2005/051452 A2 | 6/2005 |
| WO | WO-2005/055945 A2 | 6/2005 |
| WO | WO-2005/082376 A1 | 9/2005 |
| WO | WO-2005/094279 A2 | 10/2005 |
| WO | WO-2005/099715 A2 | 10/2005 |
| WO | WO-2005/110436 A2 | 11/2005 |
| WO | WO-2005/110473 A2 | 11/2005 |
| WO | WO-2006/002365 A2 | 1/2006 |
| WO | WO-2006/002366 A2 | 1/2006 |
| WO | WO-2006/002399 A2 | 1/2006 |
| WO | WO-2006/014484 A2 | 2/2006 |
| WO | WO-2006/020755 A2 | 2/2006 |
| WO | WO-2006/023627 A1 | 3/2006 |
| WO | WO-2006/026531 A1 | 3/2006 |
| WO | WO-2006/039336 A2 | 4/2006 |
| WO | WO-2006/041942 A2 | 4/2006 |
| WO | WO-2006/053007 A2 | 5/2006 |
| WO | WO-2006/086744 A1 | 8/2006 |
| WO | WO-2006/086750 A1 | 8/2006 |
| WO | WO-2006/102378 A2 | 9/2006 |
| WO | WO-2006/102378 A3 | 9/2006 |
| WO | WO-2006/108239 A1 | 10/2006 |
| WO | WO-2006/110487 A1 | 10/2006 |
| WO | WO-2006/116716 A2 | 11/2006 |
| WO | WO-2006/133052 A2 | 12/2006 |
| WO | WO-2007/011880 A2 | 1/2007 |
| WO | WO-2007/065588 A1 | 6/2007 |
| WO | WO-2007/083316 A2 | 7/2007 |
| WO | WO-2007/092620 A2 | 8/2007 |
| WO | WO-2007/112052 A2 | 10/2007 |

OTHER PUBLICATIONS

Anonymous (May 1986). "Argon Laser Photocoagulation for Neovascular Maculopathy. Three-Year results From Randomized Clinical Trials. Macular Photocoagulation Study Group," *Arch. Ophthal.* 104:694-701.

Anonymous (Sep. 1991). "Laser Photocoagulation of Subfoveal Neovascular Lesions in Age-Related Macular Degeneration. Results of a Randomized Clinical Trial. Macular Photocoagulation Study Group," *Arch. Ophthal.* 109:1220-1231.

Anonymous (Sep. 1991). "Laser Photocoagulation of Subfoveal Recurrent Neovascular Lesions in Age-Related Macular Degeneration. Results of a Randomized Clinical Trial. Macular Photocoagulation Study Group," *Arch. Ophthal.* 109:1232-1241.

Anonymous (Sep. 1991). "Subfoveal Neovascular Lesions in Age-Related Macular Degeneration. Guidelines for Evaluation and Treatment in the Macular Photocoagulation Study. Results of a Randomized Clinical Trial. Macular Photocoagulation Study Group," *Arch. Ophthal.* 109:1242-1257.

Anonymous (Oct. 1999). "Photodynamic Therapy of Subfoveal Choroidal Neovascularization in Age-Related Macular Degeneration With Verteporfin: One-Year Results of 2 Randomized Clinical Trials—TAP Report 1. Treatment of Age-Related Macular Degeneration With Photodynamic Therapy (TAP) Study Group," *Arch. Ophthal.* 117:1329-1345.

(56) References Cited

OTHER PUBLICATIONS

Raghava, S. et al. (Nov. 2004). "Periocular Routes for Retinal Drug Delivery," *Expert. Opin. Drug. Deliv.* 1(1):99-114.
Simamora, P. et al. (2001). "Solubilization of Rapamycin," *Intl. J. Pharma.* 213:25-29.
Arias, L. (2007). "Management of Diabetic Macular Edema with Antiangiogenic Therapy," *Expert Review of Ophthalmology* 2(1):23-26.
Averbukh, E. et al. (Feb. 2006). "Diabetic Macular Edema: Towards Therapy Aimed at the Underlying Pathogenic Mechanisms," *The Israel Medical Association Journal* 8:127-128.
Bertelmann, E. et al. (2004). "Immunomodulatory Therapy in Ophthalmology—Is There a Place for Topical Application?," *Ophthalmologica* 218:359-367.
Chusid, M. J. et al. (Oct. 1986). "The Role of the Polymorphonuclear Leukocyte in the Induction of Corneal Edema," *Investigative Ophthalmology & Visual Science* 27(10):1466-1469.
Ciulla, T. A. et al. (Sep. 2003). "Diabetic Retinopathy and Diabetic Macular Edema: Pathophysiology, Screening, and Novel Therapies," *Diabetes Care* 26(9):2653-2664.
Gardner, T. W. et al. (2008). "Novel Potential Mechanisms for Diabetic Macular Edema: Leveraging New Investigational Approaches," *Current Diabetes Reports* 8:263-269.
Lal, A. (1993). "Drop Volume of Commercial Anti-Glaucoma Eye Drops," *Indian Journal of Pharmacology* 25:163-164.
MacuSight, Inc. "Safety and Tolerability of MS-R001 in Patients with Diabetic Macular Edema Secondary to Diabetic Retinopathy," located at <http://clinicaltrials.gov/ct2/show/NCT00401115?term=macular+edema+and+rapamycin&rank =3> visited on Jan. 26, 2009. (3 pages).
National Eye Institute (NEI). "Sirolimus to Treat Diabetic Macular Edema," located at <http://clinicaltrials.gov/ct2/show/NCT00711490?term=macular+edema+and+rapamycin&rank =1> visited on Jan. 26, 2009. (6 pages).
Pavan-Langston, D. (1996). *Manual of Ocular Diagnosis and Therapy*. Fourth Edition, Little, Brown and Company: New York, pp. 162-165.
Treatment of Age-Related Macular Degeneration with Photodynamic Therapy (TAP) Study Group. (Apr. 2000). Correction for "Photodynamic Therapy of Subfoveal Choroidal Neovascularization in Age-Related Macular Degeneration with Verteporfin, One-Year Results of 2 Randomized Clinical Trials—TAP Report 1," *Archives of Ophthalmology* 118:488.
Extended European Search Report received for European Patent Application No. 08827362.8, mailed on Sep. 23, 2010, 8 pages.
Bradley et al., "Combination Therapy for the Treatment of Ocular Neovascularization", Angiogenesis, vol. 10, No. 2, 2007, pp. 141-148.
Chun et al., "A Pilot Study of Multiple Intravitreal Injections of Ranibizumab in Patients with Center-Involving Clinically Significant Diabetic Macular Edema", Ophthalmology, vol. 113, No. 10, Oct. 2006, pp. 1706-1712.
Eng et al., "Ranibizumab in Neovascular Age-Related Macular Degeneration", Clinical Interventions in Aging, vol. 1, No. 4, 2006, pp. 451-466.
Hikita, N., "Immunosuppressive Effect of Topical FK506 on Penetrating Keratoplasty in Rats", Journal of the Kurume Medical Association, vol. 57, No. 1, Japan, Jan. 1994, pp. 176-189, (Translation of Abstract only).
Jaissle et al., "Bevacizumab for Treatment of Macular Edema Secondary to Retinal Vein Occlusion", Ophthalmologe, vol. 103, No. 6, Jun. 2006, pp. 471-475, (Translation of Abstract only).
Kimura, Hideya, "Angiogenesis Inhibitors, Atarashii Ganka" New Ophthalmology, vol. 18, No. 7, Japan, Jul. 30, 2001, pp. 867-870.
Kulkarni et al., "Wet Age-Related Macular Degeneration", Advanced Drug Delivery Reviews, vol. 57, 2005, pp. 1994-2009.
Sloper et al., "Tacrolimus (FK506) in the Treatment of Posterior Uveitis Refractory to Cyclosporine", Ophthalmology, vol. 106, No. 4, Apr. 1999, pp. 723-728.

Zubilewicz et al., "Two Distinct Signalling Pathways are Involved in FGF2-Stimulated Proliferation of Choriocapillary Endothelial Cells: A Comparative Study with VEGF", Oncogene, vol. 20, Mar. 22, 2001, pp. 1403-1413.
United States Office Action mailed Apr. 22, 2009, for U.S. Appl. No. 11/386,290, filed Mar. 21, 2006, 13 pages.
United States Office Action mailed Apr. 3, 2008, for U.S. Appl. No. 10/665,203, filed Sep. 18, 2003, 6 pages.
United States Office Action mailed Aug. 6, 2008, for U.S. Appl. No. 11/386,290, filed Mar. 21, 2006, 8 pages.
United States Office Action mailed Feb. 7, 2008, for U.S. Appl. No. 10/945,682, filed Sep. 20, 2004, 8 pages.
United States Office Action mailed Jan. 12, 2009, for U.S. Appl. No. 10/665,203, filed Sep. 18, 2003, 6 pages.
United States Office Action mailed Jan. 29, 2009, for U.S. Appl. No. 10/945,682, filed Sep. 20, 2004, 8 pages.
United States Office Action mailed Jul. 6, 2007, for U.S. Appl. No. 10/665,203, filed Sep. 18, 2003, 4 pages.
United States Office Action mailed Jun. 11, 2009, for U.S. Appl. No. 11/726,813, filed Mar. 23, 2007, 17 pages.
United States Office Action mailed Mar. 16, 2010, for U.S. Appl. No. 11/726,813, filed Mar. 23, 2007, 12 pages.
Akselband, Y. et al. (Dec. 1991). "Rapamycin Inhibits Spontaneous and Fibroblast Growth Factor Beta-Stimulated Proliferation of Endothelial Cells and Fibroblasts," *Transplantation Proceedings* 23(6):2833-2836.
Alteheld, A. et al. (2005). "Biodegradable Amorphous Copolyester-Urethane Networks Having Shape-Memory Properties," *Angewandte Chemie International Edition* 44:1188-1192.
Apel, A. et al. (Aug. 1995). "A Subconjuctival Degradable Implant for Cyclosporine Delivery in Corneal Transplant Therapy," *Current Eye Research* 14(8):659-667.
Aramoto, H. et al. (Oct. 2004). "Vascular Endothelial Growth Factor Stimulates Differential Signaling Pathways in In Vivo Microcirculation," *American Journal of Physiology—Heart and Circulatory Physiology* 287:H1590-H1598.
Auricchio, A. et al. (Aug. 2002). "Pharmacological Regulation of Protein Expression from Adeno-Associated Viral Vectors in the Eye," *Molecular Therapy* 6(2):238-242.
Bainbridge, J. W. B. et al. (2003). "Hypoxia-Regulated Transgene Expression in Experimental Retinal Choroidal Neovascularization,"*Gene Therapy* 10:1049-1054.
Beeley, N. R. F. et al. (Mar. 15, 2006). "Development, Implantation, In Vivo Elution, and Retrieval of a Biocompatible, Sustained Release Subretinal Drug Delivery System," *Journal of Biomedical Materials Research Part A* 76A:690-698.
Behl, C. (Dec. 1997). "Amyloid Beta-Protein Toxicity and Oxidative Stress in Alzheimer's Disease," *Cell & Tissue Research* 290(3):471-480.
Bergers, G. et al. (Jun. 2003). "Tumorigenesis and the Angiogenic Switch," *Nature Reviews-Cancer* 3(6):401-410.
Bourne, R. R. et al., (1998). "Epidemic Optic Neuropathy in Primary School Children in Dar es Salaam, Tanzania," *British Journal of Ophthalmology* 82:232-234.
Bucci, M. et al. (Dec. 2000). "In Vivo Delivery of the Caveolin-1 Scaffolding Domain Inhibits Nitric Oxide Synthesis and Reduces Inflammation," *Nature Medicine* 6(12):1362-1367.
Cancer Weekly Editors. (Jan. 14, 2003). "Cancer Therapy: Study of Possible Anticancer Drug Reveals New Mechanism of Gene Regulation," Cancer Weekly via NewsRx.com and NewsRx.net, 2 pages.
Cicciarelli, N. et al. (Mar. 15, 2001). "Pharmacokinetics of Subconjunctivally Administered Cyclosporine A: Local Delivery Prior to Chemotherapy for Retinoblastoma," *IOVS*, Apr. 29-May 4, 2001, Fort Lauderdale, Florida, 42(4):S332, Abstract 1792-B42.
Edinger, A. L. et al. (Dec. 1, 2003). "Differential Effects of Rapamycin on Mammalian Target of Rapamycin Signaling Functions in Mammalian Cells," *Cancer Research* 63:8451-8460.
Geroski, D. H. et al. (2001). "Transscleral Drug Delivery for Posterior Segment Disease," *Advanced Drug Delivery Reviews* 52:37-48.
Gilbard, J. P. (Feb. 1999). "EW Interview: Electrolyte Balance is Key to Dry-eye Product's Success," *EyeWorld*, pp. 20-21.

(56) References Cited

OTHER PUBLICATIONS

Guba, M. et al. (2001). "Rapamycin Inhibits Tumor Growth and Metastasis by Antiangiogenesis," *Chirurgisches Forum 2001*, pp. 37-39. (English Abstract attached).
Guba, M. et al. (Feb. 2002). "Rapamycin Inhibits Primary and Metastatic Tumor Growth by Antiangiogenesis: Involvement of Vascular Endothelial Growth Factor," *Nature Medicine* 8(2):128-135.
Hackstein, H. et al. (Aug. 1, 2002). "Rapamycin Inhibits Macropinocytosis and Mannose Receptor-Mediated Endocytosis by Bone Marrow-Derived Dendritic Cells," *Blood* 100(3):1084-1087.
Hafizi, S. et al. (2005). "Differential Effects of Rapamycin, Cyclosporine A, and FK506 on Human Coronary Artery Smooth Muscle Cell Proliferation and Signaling," *Vascular Pharmacology* 41:167-176.
Harris, A. et al. (2001). "Implantation of a Sustained-Release Ganciclovir Implant," Chapter 45 In *Vitreoretinal Surgical Techniques*, pp. 521-531.
Hayward, C. M. et al. (Sep. 22, 1993). "Total Synthesis of Rapamycin via a Novel Titanium-Mediated Aldol Macrocyclization Reaction," *Journal of the American Chemical Society* 115(20):9345-9346.
Humar, R. et al. (2002). "Hypoxia Enhances Vascular Cell Proliferation and Angiogenesis In Vitro Via Rapamycin (mTOR)-Dependent Signaling," *The FASEB Journal* 16:771-780.
Kulkarni, P. S. (1994). "Steroidal and Nonsteroidal Drugs in Endotoxin-Induced Uveitis," *Journal of Ocular Pharmacology* 10(1)329-334.
Kuroki, A. et al. (2003). "Rapamycin Inhibits Retinal and Choroidal Neovascularization in Mice," *Investigative Ophthalmology & Visual Science* 44:E-Abstract 573, 2 pages.
Lallemand, F. et al. (2003). "Cyclosporine A Delivery to the Eye: A Pharmaceutical Challenge," *European Journal of Pharmaceutics and Biopharmaceutics* 56:307-318.
Lipner, M. (Feb. 1999). "Dry Eye 101: Developing Etiologies and Treatments for the Widespread Syndrome," *EyeWorld*, pp. 19, 21.
Marsland, A. M. et al. (Nov.-Dec. 2002). "The Macrolide Immunosuppressants in Dermatology: Mechanisms of Action," *European Journal of Dermatology* 12:618-621.
Martin, D. F. et al. (Jan. 15, 1995). "Synergistic Effect of Rapamycin and Cyclosporin A in the Treatment of Experimental Autoimmune Uveoretinitis," *The Journal of Immunology* 154(2):922-927.
Mayhan, W. G. et al. (Sep. 1984). "The Effect of Altering the External Calcium Concentration and a Calcium Channel Blocker, Verapamil, on Microvascular Leaky Sites and Dextran Clearance in the Hamster Cheek Pouch," *Microvascular Research* 28(2):159-179.
MediVas. (2007). "MediVas Announces Signing of Collaboration Agreement with Pfizer," located at <www.medivas.com/News/news_MediVas_Announces_Signing_of_Collaboration_Agreement_with_Pfizer.html> visited on Jul. 28, 2008. (1 page).
Murphy, R. P. (Mar. 1995). "Management of Diabetic Retinopathy," *American Family Physician* 51 (4):785-796.
Napoli, K. L. et al. (2001). "From Beach to Bedside: History of the Development of Sirolimus," *Therapeutic Drug Monitoring* 23(5):559-586.
Nicolaou, K. C. et al. (1993). "Total Synthesis of Rapamycin," *Journal of the American Chemical Society* 115(10):4419-4420.
Ohia, E. O. et al. (1992). "Effects of Steroids and Immunosuppressive Drugs on Endotoxin-Uveitis in Rabbits," *Journal of Ocular Pharmacology* 8(4):295-307.
Olsen, T. W. et al. (Nov. 1994). "Rapamycin Inhibits Corneal Allograft Rejection and Neovascularization," *Archives of Ophthalmology* 112:1471-1475.
Paiva, N. L. et al. (Jan.-Feb. 1991). "Incorporation of Acetate, Propionate, and Methionine into Rapamycin by *Streptomyces hygroscopicus*," *Journal of Natural Products* 54(1):167-177.
Passos, E. et al. (Mar./Apr. 2002). "Ocular Toxcity of Intravitreal Tacrolimus," *Ophthalmic Surgery and Lasers* 33(2):140-144.
Phung, T. L. et al. (Aug. 2006). "Pathological Angiogenesis is Induced by Sustained Akt Signaling and Inhibited by Rapamycin," *Cancer Cell* 10:159-170.
Renau, T. E. et al. (2003). "Conformationally-Restricted Analogues of Efflux Pump Inhibitors that Potentiate the Activity of Levofloxaxin in *Pseudomonas aeruginosa*," *Bioorganic & Medicinal Chemistry Letters* 13:2755-2758.
Renau, T. E. et al., (2001). "Addressing the Stability of C-Capped Dipeptide Efflux Pump Inhibitors that Potentiate the Activity of Levofloxacin in *Pseudomonas aeruginosa*," *Bioorganic & Medicinal Chemistry Letters* 11:663-667.
Rivera, V. M. et al. (Jul. 1999). "Long-Term Regulated Expression of Growth Hormone in Mice after Intramuscular Gene Transfer," *Proceedings of the National Academy of Sciences of the United States of America* 96:8657-8662.
Robinson, J. R. et al. (1995). "Bioadhesive and Phase-Change Polymers for Ocular Drug Delivery," *Advanced Drug Delivery Reviews* 16:45-50.
Romo, D. et al. (1993). "Total Synthesis of (−) Rapamycin Using an Evans-Tishchenko Fragment Coupling," *Journal of the American Chemical Society* 115(17):7906-7907.
Schlingemann, R. O. et al. (Jun. 1997). "Role of Vascular Permeability Factor/Vascular Endothelial Growth Factor in Eye Disease," *British Journal of Ophthalmology* 81(6):501-512.
Sehgal, S. N. et al. (Apr. 1983). "Demethoxyrapamycin (AY-24,668), A New Antifungal Antibiotic," *The Journal of Antibiotics* 36(4):351-354.
Sehgal, S. N. et al. (Oct. 1975). "Rapamycin (AY-22,989), A New Antifungal Antibiotic, II. Fermentation, Isolation and Characterization," *The Journal of Antibiotics* 28(10):727-732.
Shen, W.-Y. et al. (Jul. 2001). "Combined Effect of Cyclosporine and Sirolimus on Improving the Longevity of Recombinant Adenovirus-Mediated Transgene Expression in the Retina," *Archives of Ophthalmology* 119:1033-1043.
Spaide, R. F. et al. (Aug. 2003). "Combined Photodynamic Therapy With Verteporfin and Intravitreal Triamcinolone Acetonide for Choroidal Neovascularization," *Ophthalmology* 110(8):1517-1525.
Stepkowski, S. M. et al. (Jan. 1991). "Rapamycin, a Potent Immunosuppressive Drug for Vascularized Heart, Kidney, and Small Bowel Transplantation in the Rat," *Transplantation* 51(1):22-26.
Treins, C. et al. (Aug. 2, 2002). "Insulin Stimulates Hypoxia-Inducible Factor 1 Through a Phosphatidylinositol 3-kinase/Target of Rapamycin-Dependent Signaling Pathway," *The Journal of Biological Chemistry* 277(31):27975-27981.
Vézina, C. et al. (Oct. 1975). "Rapamycin (AY-22,989), A New Antifungal Antibiotic, I. Taxonomy of the Producing Streptomycete and Isolation of the Active Principle," *The Journal of Antibiotics* 28(10):721-726.
Wen, R. et al. (2003). "Rapamycin Inhibits Choroidal Neovascularization," *Investigative Ophthalmology & Visual Science* 44:E-Abstract 3928, 2 pages.
Extended European Search Report received for European Patent Application No. 12004712.1, mailed on Oct. 25, 2012, 13 pages.
Anonymous, "Dry AMD", retrieved from Internet on Jul. 10, 2013, <http://www.amd.org/what-is-amd/dry-amd.html>, 1 page.
Bainbridge et al., "Gene Therapy Progress and Prospects: The Eye", Gene Therapy, vol. 13, 2006, pp. 1191-1197.
Hatefi et al., "Biodegradable Injectable in Situ Forming Drug Delivery Systems", Journal of Controlled Release, vol. 80, 2002, pp. 9-28.
Kok et al., "Developments in the Treatment of Uveitis", Expert Opinion on Investigational Drugs, vol. 11, No. 1, 2002, pp. 59-67.
Serajuddin et al., "Water Migration from Soft Gelatin Capsule Shell to Fill Material and its Effect on Drug Solubility", Journal of Pharmaceutical Sciences, vol. 75, No. 1, Jan. 1986, pp. 62-64.
Whiting et al., "The Effect of Rapamycin on Renal Function in the Rat: A Comparative Study with Cyclosporine", Toxicology Letters, vol. 58, 1991, pp. 169-179.

\* cited by examiner

Figure 1

RAPAMYCIN FORMULATIONS AND METHODS OF THEIR USE

CROSS-REFERENCES TO RELATED APPLICATIONS

The present application is related to and claims priority from U.S. Provisional Patent Application Ser. No. 60/664,040 titled "Liquid Formulations For Treatment Of Diseases Or Conditions," filed Mar. 21, 2005, U.S. Provisional Patent Application Ser. No. 60/664,306 titled "In Situ Gelling Formulations And Liquid Formulations For Treatment of Diseases Or Conditions," filed Mar. 21, 2005, U.S. Provisional Patent Application Ser. No. 60/651,790, titled "Formulations For Ocular Treatment," filed Feb. 9, 2005, each of which is incorporated herein by reference in its entirety for all purposes.

FIELD

Described herein are liquid rapamycin formulations for treatment or prevention of age-related macular degeneration ("AMD"), by delivery of the liquid rapamycin formulation to the eye of a subject, including but not limited to a human subject.

BACKGROUND

The retina of the eye contains the cones and rods that detect light. In the center of the retina is the macula lutea, which is about ⅓ to ½ cm in diameter. The macula provides detailed vision, particularly in the center (the fovea), because the cones are higher in density. Blood vessels, ganglion cells, inner nuclear layer and cells, and the plexiform layers are all displaced to one side (rather than resting above the cones), thereby allowing light a more direct path to the cones.

Under the retina are the choroid, comprising a collection of blood vessels embedded within a fibrous tissue, and the deeply pigmented epithelium, which overlays the choroid layer. The choroidal blood vessels provide nutrition to the retina (particularly its visual cells).

There are a variety of retinal disorders for which there is currently no treatment or for which the current treatment is not optimal. Macular degeneration and choroidal neovascularization are nonlimiting examples of retinal disorders that are difficult to treat with conventional therapies.

Age-related macular degeneration (AMD) is the major cause of severe visual loss in the United States for individuals over the age of 60. AMD occurs in either an atrophic or less commonly an exudative form. The atrophic form of AMD is also called "dry AMD," and the exudative form of AMD is also called "wet AMD."

In exudative AMD, blood vessels grow from the choriocapillaris through defects in Bruch's membrane, and in some cases the underlying retinal pigment epithelium. Organization of serous or hemorrhagic exudates escaping from these vessels results in fibrovascular scarring of the macular region with attendant degeneration of the neuroretina, detachment and tears of the retinal pigment epithelium, vitreous hemorrhage and permanent loss of central vision. This process is responsible for more than 80% of cases of significant visual loss in subjects with AMD. Current or forthcoming treatments include laser photocoagulation, photodynamic therapy, treatment with pegylated aptamers, treatment with VEGF antibody fragments, and treatment with certain small molecule agents.

Several studies have recently described the use of laser photocoagulation in the treatment of initial or recurrent neovascular lesions associated with AMD (Macular Photocoagulation Study Groups (1991) in *Arch. Ophthal.* 109:1220; *Arch. Ophthal.* 109:1232; *Arch. Ophthal.* 109:1242). Unfortunately, AMD subjects with subfoveal lesions subjected to laser treatment experienced a rather precipitous reduction in visual acuity (mean 3 lines) at 3 months follow-up. Moreover, at two years post-treatment treated eyes had only marginally better visual acuity than their untreated counterparts (means of 20/320 and 20/400, respectively). Another drawback of the procedure is that vision after surgery is immediately worse.

Photodynamic therapy (PDT) is a form of phototherapy, a term encompassing all treatments that use light to produce a beneficial reaction in a subject. Optimally, PDT destroys unwanted tissue while sparing norm al tissue. Typically, a compound called a photosensitizer is administered to the subject. Usually, the photosensitizer alone has little or no effect on the subject. When light, often from a laser, is directed onto a tissue containing the photosensitizer, the photosensitizer is activated and begins destroying targeted tissue. Because the light provided to the subject is confined to a particularly targeted area, PDT can be used to selectively target abnormal tissue, thus sparing surrounding healthy tissue. PDT is currently used to treat retinal diseases such as AMD. PDT is currently the mainstay of treatment for subfoveal choroidal neovascularization in subjects with AMD (Photodynamic Therapy for Subfoveal Choroidal Neovascularization in Age Related Macular Degeneration with Verteporfin (TAP Study Group) *Arch Ophthalmol.* 1999 117:1329-1345.

Choroidal neovascularization (CNV) has proven to be recalcitrant to treatment in most cases. Conventional laser treatment can ablate CNV and help to preserve vision in selected cases not involving the center of the retina, but this is limited to only about 10% of the cases. Unfortunately, even with successful conventional laser photocoagulation, the neovascularization recurs in about 50-70% of eyes (50% over 3 years and >60% at 5 years). (Macular Photocoagulation Study Group, *Arch. Ophthalmol.* 204:694-701 (1986)). In addition, many subjects who develop CNV are not good candidates for laser therapy because the CNV is too large for laser treatment, or the location cannot be determined so that the physician cannot accurately aim the laser. Photodynamic therapy, although utilized in up to 50% of new cases of subfoveal CNV has only marginal benefits over natural history, and generally delays progression of visual loss rather than improving vision which is already decreased secondary to the subfoveal lesion. PDT is neither preventive or definitive. Several PDT treatments are usually required per subject and additionally, certain subtypes of CNV fare less well than others.

Thus, there remains a need for methods, compositions, and formulations that may be used to optimally prevent or significantly inhibit choroidal neovascularization and to prevent and treat AMD in its wet and dry forms.

In addition to AMD, choroidal neovascularization is associated with such retinal disorders as presumed ocular histoplasmosis syndrome, myopic degeneration, angioid streaks, idiopathic central serous chorioretinopathy, inflammatory conditions of the retina and or choroid, and ocular trauma. Angiogenic damage associated with neovascularization occurs in a wide range of disorders including diabetic retinopathy, venous occlusions, sickle cell retinopathy, retinopathy of prematurity, retinal detachment, ocular ischemia and trauma.

There have been many attempts to treat CNV and its related diseases and conditions, as well as other conditions such as macular edema and chronic inflammation, with pharmaceuticals. For example, use of rapamycin to inhibit CNV and wet AMD has been described in U.S. application Ser. No. 10/665,203, which is incorporated herein by reference in its entirety. The use of rapamycin to treat inflammatory diseases of the eye has been described in U.S. Pat. No. 5,387,589, titled Method of Treating Ocular Inflammation, with inventor Prassad Kulkarni, assigned to University of Louisville Research Foundation, the contents of which is incorporated herein by reference in its entirety. U.S. Pat. App. Nos. 60/503,840 and Ser. No. 10/945,682 are further incorporated herein by reference in their respective entireties. Another reference whose contents are incorporated herein by reference in its entirety is U.S. Pat. No. 6,376,517.

Particularly for chronic diseases, including those described herein, there is a great need for long acting methods for delivering therapeutic agents to the eye, such as to the posterior segment to treat CNV in such diseases as AMD. Formulations with extended delivery of therapeutic agent are more comfortable and convenient for a subject, due to a diminished frequency of ocular injections of the therapeutic agent.

Direct delivery of therapeutic agents to the eye rather than systemic administration may be advantageous because the therapeutic agent concentration at the site of action is increased relative to the therapeutic agent concentration in a subject's circulatory system. Additionally, therapeutic agents may have undesirable side effects when delivered systemically to treat posterior segment disease. Thus, localized drug delivery may promote efficacy while decreasing side effects and systemic toxicity.

SUMMARY

The methods and liquid rapamycin formulations described herein allow delivery of rapamycin to the eye of a subject. Unless the context indicates otherwise, it is envisioned that the subjects on whom all of the methods of treatment may be performed include human subjects.

Described herein are methods and liquid rapamycin formulations for delivering rapamycin for extended periods of time which can be used for the treatment, prevention, inhibition, delaying onset of, or causing regression of diseases and conditions including CNV, wet AMD, and dry AMD.

As described in further detail in the Detailed Description section, the methods and liquid rapamycin formulations may also be used for delivery to a subject or to the eye of a subject of therapeutically effective amounts of rapamycin for the treatment, prevention, inhibition, delaying of the onset of, or causing the regression of wet or dry AMD. In some variations, the methods, compositions;.and liquid formulations are used to treat wet AMD. In some variations, the methods, compositions, and liquid formulations are used to prevent wet AMD. In some variations, the methods, compositions, and liquid formulations are used to treat dry AMD. In some variations, the methods, compositions, and liquid formulations are used to prevent dry AMD. In some variations, the methods, compositions, and liquid formulations are used to prevent transition from dry AMD to wet AMD. The methods, compositions and liquid formulations may also be used for delivery to a subject or to the eye of a subject of therapeutically effective amounts of rapamycin for the treatment, prevention, inhibition, delaying of the onset of, or causing the regression of CNV. In some variations, the methods, compositions and liquid formulations are used to treat CNV. The methods, compositions and liquid formulations may also be used for delivery to a subject or to the eye of a subject of therapeutically effective amounts of rapamycin for the treatment, prevention, inhibition, delaying of the onset of, or causing the regression of angiogenesis in the eye. In some variations, the methods, compositions and liquid formulations are used to treat angiogenesis. Other diseases and conditions that may be treated, prevented, inhibited, have onset delayed, or caused to regress using rapamycin are described in the Diseases and Conditions section of the Detailed Description.

In some variations, the liquid formulations described herein form a non-dispersed mass when placed into a rabbit eye, including but not limited to the vitreous of a rabbit eye.

The liquid rapamycin formulations may generally be administered in any volume that has the desired effect. In some variations a volume of a liquid rapamycin formulation is administered to the vitreous and the liquid formulation is less than one half the volume of the vitreous. In some variations, formation of a non-dispersed mass after placement of the liquid rapamycin formulation in a rabbit eye r a subject depends upon the volume of the liquid rapamycin formulation injected or placed in the rabbit eye or subject. The liquid rapamycin formulations described herein are generally administered intraocularly, periocularly, intravitreally, or between the sclera and conjunctiva.

The liquid rapamycin formulations described herein may deliver rapamycin for an extended period of time. One non-limiting example of such an extended release delivery system is a liquid rapamycin formulation that delivers rapamycin to the eye of human a subject in an amount sufficient to treat, prevent, inhibit, delay onset of, or cause regression of wet or dry AMD, or CNV, in a subject for an extended period of time. In some variations, the liquid rapamycin formulation is used to treat wet or dry AMD or CNV in a human subject. In some variations, the liquid rapamycin formulation is used to prevent transition of dry AMD to wet AMD in a human subject. In some variations, the liquid rapamycin formulation delivers an amount of rapamycin effect to treat or prevent wet or dry AMD or CNV for at least about one, about two, about three, about six, about nine, or about twelve months. Other extended periods of release are described in the Detailed Description.

Described herein is a liquid formulation comprising about 2% (w/w) of rapamycin, about 94% (w/w) PEG 400, and about 4% (w/w) of ethanol. Described herein is a method for treating wet age-related macular degeneration in a human subject, the method comprising administering to the human subject by intraocular or periocular delivery a volume of a liquid formulation comprising about 2% (w/w) of rapamycin, about 94% (w/w) PEG 400, and about 4% (w/w) of ethanol containing an amount of rapamycin effective to treat wet age-related macular degeneration in the human subject. Described herein is a method for preventing wet age-related macular degeneration in a human subject, the method comprising administering to the human subject by intraocular or periocular delivery a volume of a liquid formulation comprising about 2% (w/w) of rapamycin, about 94% (w/w) PEG 400, and about 4% (w/w) of ethanol containing an amount of rapamycin effective to prevent wet age-related macular degeneration in the human subject. In some variations the human subject is identified as being at heightened risk of developing wet age-related macular degeneration in the eye to which the liquid formulation is administered. In some variations the human subject has dry age-related macular degeneration in at least one eye. In some variations the human subject has wet age-related macular degeneration in one eye and the liquid formulation is administered to the eye without wet age-related macular degeneration.

Described herein are methods for treating dry age-related macular degeneration in a human subject comprising administering to the human subject by intraocular or periocular delivery a volume of a liquid formulation comprising about 2% (w/w) of rapamycin, about 94% (w/w) PEG 400, and about 4% (w/w) of ethanol.

Described herein are methods for preventing wet age-related macular degeneration in a human subject having dry age-related macular degeneration, the method comprising administering to a human subject having dry age-related macular degeneration a volume of a liquid formulation comprising about 2% (w/w) of rapamycin, about 94% (w/w) PEG 400, and about 4% (w/w) of ethanol, wherein the volume is administered by intraocular or periocular delivery.

In some variations, the volume of a liquid formulation is administered to the human subject by placement in the vitreous and the volume of liquid formulation contains less than about 3 mg of rapamycin. In some variations, the volume of liquid formulation contains less than about 2.5 mg of rapamycin. In some variations, the volume of liquid formulation contains less than about 2 mg of rapamycin. In some variations, the volume of liquid formulation contains between about 20 μg and about 2.5 mg of rapamycin. In some variations, the volume of liquid formulation is administered to the human subject by placement between the sclera and conjunctiva and the volume of liquid formulation contains less than about 5 mg of rapamycin. In some variations, the volume of liquid formulation contains less than about 3.5 mg of rapamycin. In some variations, the volume of liquid formulation contains less than about 3 mg of rapamycin. In some variations, the volume of liquid formulation contains between about 20 μg and about 5 mg of rapamycin.

In some variations, the volume of liquid formulation is administered to the human subject by placement in the vitreous of the human subject and the volume of liquid formulation contains less than about 100 μL of PEG 400. In some variations, the volume of liquid formulation contains less than about 50 μL of PEG 400. In some variations, wherein the volume of liquid formulation contains less than about 30 μL of PEG 400.

In some variations, the volume of liquid formulation is administered to the human subject by placement between the sclera and conjunctiva and the volume of liquid formulation contains less than about 160 μL of PEG 400. In some variations, the volume of liquid formulation contains less than about 120 μL of PEG 400. In some variations, wherein the volume of liquid formulation contains less than about 90 μL of PEG 400.

In some variations, a volume of a liquid formulation described herein of less than about 50 μL of liquid formulation is administered to the human subject by placement in the vitreous of the human subject. In some variations, a volume of less than about 20 μL of liquid formulation is administered to the human subject. In some variations, a volume of less than about 10 μL of liquid formulation is administered to the human subject. In some variations, a volume of less than about 5 μL of liquid formulation is administered to the human subject. In some variations, a volume of less than about 1 μL of liquid formulation is administered to the human subject.

In some variations, a volume of less than about 200 μL of liquid formulation is administered to the human subject by placement between the sclera and conjunctiva of the human subject. In some variations, a volume of less than about 100 μL of liquid formulation is administered to the human subject. In some variations, a volume of less than about 50 μL of liquid formulation is administered to the human subject. In some variations, a volume of less than about 20 μL of liquid formulation is administered to the human subject. In some variations, a volume of less than about 10 μL of liquid formulation is administered to the human subject. In some variations, a volume of less than about 5 μL of liquid formulation is administered to the human subject.

In some variations, a volume of a liquid formulation is administered to the human subject by placement between the sclera and conjunctiva and the human subject to which the volume is administered has visual acuity of at least about 20/40. In some variations, the human subject to which the volume is administered has visual acuity of at least about 20/40 in the eye to which the volume is administered.

Described herein are liquid formulations comprising rapamycin, a non-aqueous liquid component, and optionally a water component, wherein the rapamycin is at least about 0.1% (w/w) of the liquid formulation and the non-aqueous liquid component is at least about 90% (w/w) of the liquid formulation; and wherein the liquid formulation when injected into the vitreous of a rabbit eye delivers an amount of rapamycin sufficient to achieve an average concentration of rapamycin in the retina choroid of the rabbit eye of at least about 0.01 ng/mg for a period of time of at least about 30 or at least about 120 days following administration of the liquid formulation. In some variations, the liquid formulation when injected into the vitreous of a rabbit eye delivers an amount of rapamycin sufficient to achieve an average concentration of rapamycin in the retina choroid of the rabbit eye of at least about 0.1 ng/mg for a period of time of at least about 30 or at least about 90 days following administration of the liquid formulation.

Described herein are liquid formulations comprising rapamycin, a non-aqueous liquid component, and optionally a water component, wherein the rapamycin is at least about 0.1% (w/w) of the liquid formulation and the non-aqueous liquid component is at least about 90% (w/w) of the liquid formulation; and wherein the liquid formulation when injected into the vitreous of a rabbit eye delivers an amount of rapamycin sufficient to achieve an average concentration of rapamycin in the vitreous of the rabbit eye of at least about 1000 ng/ml for a period of time of at least about 30 or at least about 120 days following administration of the liquid formulation.

Described herein are liquid formulations comprising rapamycin, a non-aqueous liquid component, and optionally a water component, wherein the rapamycin is at least about 0.1% (w/w) of the liquid formulation and the non-aqueous liquid component is at least about 90% (w/w) of the liquid formulation; and wherein the liquid formulation when injected between the sclera and conjunctiva of a rabbit eye delivers an amount of rapamycin sufficient to achieve an average concentration of rapamycin in the vitreous of the rabbit eye of at least about 0.01 ng/ml for a period of time of at least about 30 or at least about 120 days following administration of the liquid formulation. In some variations, the liquid formulation when injected between the sclera and conjunctiva of a rabbit eye delivers an amount of rapamycin sufficient to achieve an average concentration of rapamycin in the vitreous of the rabbit eye of at least about 0.1 ng/ml for a period of time of at least about 30 or at least about 120 days following administration of the liquid formulation.

Described herein are liquid formulations comprising rapamycin, a non-aqueous liquid component, and optionally a water component, wherein the rapamycin is at least about 0.1% (w/w) of the liquid formulation and the non-aqueous liquid component is at least about 90% (w/w) of the liquid formulation; and wherein the liquid formulation when injected between the sclera and conjunctiva of a rabbit eye delivers an amount of rapamycin sufficient to achieve an average concentration of rapamycin in the retina choroid of the rabbit eye of at least about 0.001 ng/mg for a period of time of at least about 30 or at least about 120 days following administration of the liquid formulation. In some variations, the liquid formulation when injected between the sclera and conjunctiva of a rabbit eye delivers an amount of rapamycin sufficient to achieve an average concentration of rapamycin in the retina choroid of the rabbit eye of at least about 0.005 ng/mg for a period of time of at least about 30 or at least about 120 days following administration of the liquid formulation. In some variations, the liquid formulation when injected between the sclera and conjunctiva of a rabbit eye delivers an amount of rapamycin sufficient to achieve an average concentration of rapamycin in the retina choroid of the rabbit eye of at least about 0.01 ng/mg for a period of time of at least about 30 days following administration of the liquid formulation.

Described herein are liquid formulations wherein the rapamycin is less than about 6% (w/w) of the liquid formulation, the water component is less than about 5% (w/w) of the liquid formulation, and the non-aqueous liquid component is selected from the group consisting of any one or more of glycerin, dimethylsulfoxide, N-methylpyrrolidone, dimethyl acetamide (DMA), dimethyl formamide;,glycerol formal, ethoxy diglycol, triethylene glycol dimethyl ether, triacetin, diacetin, corn oil, acetyl triethyl citrate (ATC), ethyl lactate, polyglycolated capryl glyceride, γ butrolactone, dimethyl isosorbide, or benzyl alcohol.

Described herein are unit dosage forms comprising a volume of a liquid formulation as described herein, wherein the volume of liquid formulation contains less than about 4 mg, less than about 3.5 mg, less than about 3 mg, less than about 2.5 mg, less than about 2 mg, between about 20 µg and about 2.5 mg, or between about 20 µg and about 5 mg of rapamycin.

Described herein are unit dosage forms comprising a volume of a liquid formulation as described herein, wherein the non-aqueous liquid component is polyethylene glycol and the volume of liquid formulation contains less than about 160 µL, less than about 120 µL, less than about 90 µL, less than about 50 µL of polyethylene glycol, or less than about 30 µL of polyethylene glycol.

Described herein are unit dosage forms comprising a volume of less than about 200 µL, less than about 100 µL, less than about 50 µL, less than about 20 µL, less than about 10 µL, less than about 5 µL, or less than about 1 µL of a liquid formulation described herein.

Described herein are methods for treating wet age-related macular degeneration in a human subject, the method comprising administering to the human subject by intraocular or periocular delivery a volume of a liquid formulation described herein containing an amount of rapamycin effective to treat wet age-related macular degeneration in the human subject.

Described herein are methods for preventing wet age-related macular degeneration in a human subject, the method comprising administering to the human subject by intraocular or periocular delivery a volume of the liquid formulation described herein containing an amount of rapamycin effective to prevent wet age-related macular degeneration in the human subject. In some variations the human subject is identified as being at heightened risk of developing wet age-related macular degeneration in the eye to which the liquid formulation is administered. In some variations the human subject identified as being at heightened risk of developing wet age-related macular degeneration has dry age-related macular degeneration in at least one eye. In some variations the human subject identified as being at heightened risk of developing wet age-related macular degeneration has wet age-related macular degeneration in one eye and the liquid formulation is administered to the eye without wet age-related macular degeneration.

Described herein are methods for treating dry age-related macular degeneration in a human subject, the method comprising administering to the human subject by intraocular or periocular delivery a volume of a liquid formulation described herein containing an amount of rapamycin effective to treat dry age-related macular degeneration in the human subject.

Described herein are methods for preventing wet age-related macular degeneration in a human subject having dry age-related macular degeneration, the method comprising administering to a human subject having dry age-related macular degeneration a volume of a liquid formulation described herein containing an amount of rapamycin effective to prevent wet age-related macular degeneration in the human subject, wherein the volume of the liquid formulation is administered by intraocular or periocular delivery.

DETAILED DESCRIPTION

Figure 1A:
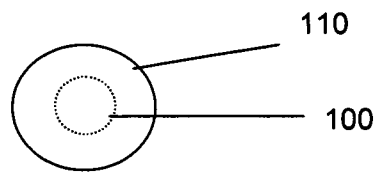
FIGS. 1A-1C schematically depict formation of a non-dispersed mass, after injection of a liquid formulation into the vitreous of an eye, as it is believed to occur in some variations.

Described in this section are liquid rapamycin formulations and methods relating to delivery of rapamycin to a subject or to the eye of a subject. These liquid rapamycin formulations and methods may be used for the treatment, prevention, inhibition, delaying onset of, or causing regression of diseases and conditions of the eye including but not limited to choroidal neovascularization; macular degeneration and age-related macular degeneration, including wet AMD and dry AMD. In some variations, the liquid rapamycin formulations and methods are used for treatment of choroidal neovascularization; macular degeneration and age-related macular degeneration, including wet AMD and dry AMD. In some variations, the liquid rapamycin formulations and methods are used for prevention of choroidal neovascularization; macular degeneration and age-related macular degeneration, including wet AMD and dry AMD.

In this detailed description section are described (1) liquid rapamycin formulations, (2) extended delivery of rapamycin, (3) routes of administration for delivery of liquid rapamycin formulations, and (4) treatment and prevention of CNV and wet and dry AMD by delivery of rapamycin to a subject or to the eye of a subject for an extended period of time using the described liquid rapamycin formulations.

The term "about," as used herein, generally refers to the level of accuracy that is obtained when the methods described herein, such as the methods in the examples, are used. However, by "about" a certain amount of a component of a formulation is meant 90-110% of the amount stated.

Liquid Rapamycin Formulations

The terms rapamycin and rapa are used interchangeably herein with the term sirolimus. In some variations the liquid rapamycin formulations form a non-dispersed mass relative to a surrounding medium when placed in the vitreous of a rabbit eye.

The liquid formulations described herein contain rapamycin and may generally be any liquid formulation, including but not limited to solutions, suspensions, and emulsions.

The liquid rapamycin formulations may generally be administered in any volume that has the desired effect; in some variations a liquid rapamycin formulation is administered to the vitreous and the liquid rapamycin formulation is less than one half the volume of the vitreous of the eye to which it is being administered. In some variations the liquid rapamycin formulation is administered between the sclera and conjunctiva in a volume less than about 50 µl.

When a certain volume is administered, it is understood that there is some imprecision in the accuracy of various devices that may be used to administer the liquid formulation. Where a certain volume is specified, it is understood that this is the target volume. However, certain devices such as insulin syringes are inaccurate to greater than 10%, and sometimes inaccurate to greater than 20% or more. Hamilton HPLC type syringes are generally considered precise to within 10%, and are recommended for volumes at or below 10 µl.

In some variations, a volume of a liquid rapamycin formulation described herein is administered to the vitreous of a human subject's eye that is less than about 500 µl, less than about 400 µl, less than about 300 µl, less than about 200 µl, less than about 100 µl, less than about 90 µl, less than about 80 µl, less than about 70 µl, less than about 60 µl, less than about 50 µl, less than about 40 µl, less than about 30 µl, less than about 20 µl, less than about 10 µl, less than about 5 µl, less than about 3 µl, or less than about 1 µl. In some variations, a volume of a liquid rapamycin formulation described herein is administered to the vitreous of a human subject's eye that is less than about 20 µl. In some variations, a volume of a liquid rapamycin formulation described herein is administered to the vitreous that is less than about 10 µl. In some variations, a volume of a liquid rapamycin formulation described herein is administered to the vitreous of a human subject's eye that is between about 0.1 µl and about 200 µl, between about 50 µl and about 200 µl, between about 50 µl and about 150 µl, between about 0.1 µl and about 100 µl, between about 0.1 µl and about 50 µl, between about 1 µl and about 40 µl, between about 1 µl and about 30 µl, between about 1 µl and about 20 µl, between about 1 µl and about 10 µl, or between about 1 µl and about 5 µl. In some variations, a volume of a liquid rapamycin formulation described herein is administered to the vitreous of a human subject's eye that is between about 1 µl and about 10 µl. In some variations, a volume of a liquid rapamycin formulation described herein is administered to the vitreous of a rabbit eye or a subject's eye that is between about 1 µl and about 5 µl. In some variations, a volume of a liquid rapamycin formulation described herein is administered to the vitreous of a rabbit eye or a subject's eye that is between about 1 µl and about 5 µl. In some variations, a volume of a liquid rapamycin formulation described herein is administered to the vitreous of a human subject's eye that is between about 0.1 µl and about 200 µl.

In some variations, a total volume of a liquid rapamycin formulation described herein is subconjunctivally administered to a human subject's eye that is less than about 1000 µl, less than about 900 µl, less than about 800 µl, less than about 700 µl, less than about 600 µl, less than about 500 µl, less than about 400 µl, less than about 300 µl, less than about 200 µl, less than about 100 µl, less than about 90 µl, less than about 80 µl, less than about 70 µl, less than about 60 µl, less than about 50 µl, less than about 40 µl, less than about 30 µl, less than about 20 µl, less than about 10 µl, less than about 5 µl, less than about 3 µl, or less than about 1 µl. In some variations, a volume of a liquid rapamycin formulation described herein is subconjunctivally administered to a human subject's eye that is less than about 20 µl. In some variations, a volume of a liquid rapamycin formulation described herein is subconjunctivally administered to a human subject's eye that is less than about 10 µl. In some variations, a volume of a liquid rapamycin formulation described herein is subconjunctivally administered to a human subject's eye that is between about 0.1 µl and about 200 µl, between about 50 µl and about 200 µl, between about 200 µl and about 300 µl, between about 300 µl and about 400 µl, between about 400 µl and about 500 µl, between about 500 µl and about 600 µl, between about 600 µl and about 700 µl, between about 700 µl and about 800 µl, between about 800 µl and about 900 µl, between about 900 µl and about 1000 µl, between about 50 µl and about 150 µl, between about 0.1 µl and about 100 µl, between about 0.1 µl and about 50 µl, between about 1 µl and about 40 µl, between about 1 µl and about 30 µl, between about 1 µl and about 20 µl, between about 1 µl and about 10 µl, or between about 1 µl and about 5 µl. In some variations, a volume of a liquid rapamycin formulation described herein is subconjunctivally administered to a human subject's eye that is between about 1 µl and about 10 µl. In some variations, a volume of a liquid rapamycin formulation described herein is subconjunctivally administered to a human subject's eye that is between about 1 µl and about 5 µl. In some variations, a volume of a liquid rapamycin formulation described herein is administered to subconjunctivally administered to a human subject's eye that is between about 1 µl and about 5 µl. In some, variations, a volume of a liquid rapamycin formulation described herein is administered to subconjunctivally administered to a human subject's eye that is between about 0.1 µl and about 200 µl.

In some variations the liquid rapamycin formulations described herein contain no greater than about 250 µl of polyethylene glycol. In some variations the liquid rapamycin formulation described herein contain no greater than about 250 µl, no greater than about 200 µl, no greater than about 150 µl, no greater than about 125 µl, no greater than about 100 µl, no greater than about 75 µl, no greater than about 50 µl, no greater than about 25 µl, no greater than about 20 µl, no greater than about 15 µl, no greater than about 10 µl, no greater than about 7.5 µl, no greater than about 5 µl, no greater than about 2.5 µl, no greater than about 1.0 µl, or no greater than about 0.5 µl of polyethylene glycol. Formulations containing polyethylene glycol may contain, for example, PEG 300 or PEG 400.

In some variations, the liquid rapamycin formulation described herein have a viscosity of between 40% and 120% centipoise. In some variations the liquid rapamycin formulations described herein have a viscosity of between 60% and 80% centipoise.

In some variations the liquid rapamycin formulations described herein are administered in multiple subconjunctival locations within a period of time of one another, including but not limited to within an hour of one another. Without being bound by theory, it is thought that such multiple administrations, such as multiple injections, allow for a greater total dose to be administered subconjunctivally than a single dose due to a potentially limited ability of the local ocular tissues to absorb larger volumes.

Some liquid rapamycin formulations described herein comprise a non-aqueous liquid component. The non-aqueous liquid component may comprise a single non-aqueous liquid component or a combination of non-aqueous liquid component. In some variations, the non-aqueous liquid component is glycerin, dimethylsulfoxide, N-methylpyrrolidone, ethanol, isopropyl alcohol, polyethylene glycol of various molecular weights, including but not limited to PEG 300 and PEG 400, or propylene glycol, or a mixture of one or more thereof.

Liquid rapamycin formulations may optionally further comprise stabilizers, excipients, gelling agents, adjuvants, antioxidants, and/or other components as described herein.

In some variations all components in the liquid formulation, other than the therapeutic agent, are liquid at room temperature.

In some variations the rapamycin in the liquid formulation contains between about 0.01 to about 10% of the total weight of the composition; between about 0.05 to about 10%; between about 0.1 to about 5%; between about 1 to about 5%; or between about 5 to about 15%; between about 8 to about 10%; between about 0.01 to about 1%; between about 0.05 to about 5%; between about 0.1 to about 0.2%; between about 0.2 to about 0.3%; between about 0.3 to about 0.4%; between about 0.4 to about 0.5%; between about 0.5 to about 0.6%; between about 0.6 to about 0.7%; between about 0.7 to about 1%; between about 1 to about 3%; or between about 1.5 to about 2.5%. In some variations the liquid formulations described herein contain between about 0.1 to about 5% w/w of rapamycin.

In some variations the non-aqueous liquid component is, by way of nonlimiting example, between about 0.01 to about 99.9% of the total weight of the composition; between about 0.1 to about 99%; between about 75 to about 99.99%; between about 85 to about 99.99%; or between about 55 to about 95% w/w. In some variations the non-aqueous liquid component is between about 85 to about 99.99% w/w.

In some variations there is optionally a water component. In some variations the water component is less than about 30%, less than about 25%, less than about 20%, less than about 15%, less than about 10%, less than about 7.5%, less than about 5%, less than about 4%, less than about 3%, less than about 2%, less than about 1%, or less than about 0.5%. In some variations the water component is less than about 5% w/w.

Some variations of liquid formulations includes rapamycin between about 0.01 and about 5% by weight of the total, and a non-aqueous liquid component between about 95% and about 99.99% by weight of the total. In some variations the formulations further comprise stabilizing agents, excipients, adjuvants, or antioxidants, between about 0 and about 5% by weight of the total.

In some variations, a liquid formulation may contain about 2% w/w rapamycin and about 98% w/w of a non-aqueous liquid component. In some variations, the non-aqueous liquid component comprises ethanol. In some variations, the non-aqueous liquid component comprises a liquid polyethylenely but not limited to PEG 400.

Non-aqueous liquid components that may be used include but are not limited to any non-aqueous liquid component as above, including but not limited to any one or more of DMSO, glycerin, ethanol, methanol, isopropyl alcohol; castor oil, propylene glycol, polyvinylpropylene, polysorbate 80, benzyl alcohol, dimethyl acetamide (DMA), dimethyl formamide (DMF), glycerol formal, ethoxy diglycol (Transcutol, Gattefosse), tryethylene glycol dimethyl ether (Triglyme), dimethyl isosorbide (DMI), γ-butyrolactone, N-Methyl-2-pyrrolidinone (NMP), polyethylene glycol of various molecular weights, including but not limited to PEG 300 and PEG 400, and polyglycolated capryl glyceride (Labrasol, Gattefosse).

Further non-aqueous liquid components include but are not limited to $C_6$-$C_{24}$ fatty acids, oleic acid, Imwitor 742, Capmul, F68, F68 (Lutrol), PLURONICS including but not limited to PLURONICS F108, F127, and F68, Poloxamers, Jeffamines), Tetronics, F127, beta-cyclodextrin, CMC, polysorbitan 20, Cavitron, softigen 767, captisol, and sesame oil.

Other methods that may be used to dissolve rapamycin are described in Solubilization of Rapamycin, P. Simamora et al. *Int'l J Pharma* 213 (2001) 25-29, the contents of which is incorporated herein in its entirety.

As a nonlimiting example, rapamycin can be dissolved in 5% DMSO or methanol in a balanced salt solution. The rapamycin solution can be unsaturated, a saturated or a supersaturated solution of rapamycin. The rapamycin solution can be in contact with solid rapamycin. In one nonlimiting example, rapamycin can be dissolved in a concentration of up to about 400 mg/ml. Rapamycin can also, for example, be dissolved in propylene glycol esterified with fatty acids such as oleic, stearic, palmic, capric, linoleic, etc.

Many other non-aqueous liquid components are possible. Those of ordinary skill in the art, given the teachings herein will find it routine to identify non-aqueous liquid components for use in the liquid rapamycin formulations described herein.

Non-aqueous liquid components for use in the liquid formulations can be determined by a variety of methods known in the art, including but not limited to (1) theoretically estimating their solubility parameter values and choosing the ones that match with the therapeutic agent, using standard equations in the field; and (2) experimentally determining the saturation solubility of therapeutic agent in the non-aqueous liquid components, and choosing the one(s) that exhibit the desired solubility.

In some variations, the liquid rapamycin formulations form a non-dispersed mass when placed into an aqueous medium. As used herein, a "non-dispersed mass" refers to the structure formed when the liquid formulation is placed into an environment, relative to the environment in which it is placed. Generally, a non-dispersed mass of a liquid formulation is anything other than a homogeneous distribution of the liquid formulation in the surrounding medium. The non-dispersed mass may, for instance, be indicated by visually inspecting the administered liquid formulation and characterizing its appearance relative to the surrounding medium.

In some variations, the aqueous medium is water. In some variations, the water is deionized, distilled, sterile, or tap water, including but not limited to tap water available at the place of business of MacuSight in Union City, Calif.

In some variations, the aqueous medium is an aqueous medium of a subject. In some variations the aqueous medium is an aqueous medium of the eye of a subject, including but not limited to the vitreous of an eye of a subject. In some variations the subject is a human subject. In some variations the aqueous medium is the vitreous of a rabbit eye.

The liquid formulations described herein may generally be of any geometry or shape after administration to a subject or the eye of a subject. The non-dispersed mass-forming liquid formulations may, for instance, appear as a compact spherical mass when administered to the vitreous. In other instances, the liquid formulation may appear as a non-dispersed mass relative to the surrounding medium, wherein the non-dispersed mass is less clearly defined and the geometry is more amorphous than spherical.

The non-dispersed mass-forming liquid formulations described herein may form a non-dispersed mass immediately upon placement in the medium or the non-dispersed mass may form some period of time after placement of the liquid formulation. In some variations the non-dispersed mass forms over the course of about 1, about 2, about 3, about 4, about 5, about 6, or about 7 days. In some variations the non-dispersed mass forms over the course of about 1 week, about 2 weeks, or about 3 weeks.

In some variations the liquid formulations described herein form a non-dispersed mass which has the form of a solid depot when the formulation is injected into any or all of water, the vitreous, or between the sclera and the conjunctiva of a rabbit eye. In some variations the liquid formulations described herein form a non-dispersed mass which has the form of a semi-solid when the formulation is injected into any or all of water, the vitreous, or between the sclera and the conjunctiva of a rabbit eye.

In some variations described herein the liquid rapamycin formulation forms a non-dispersed mass relative to a surrounding medium where the surrounding medium is aqueous. An "aqueous medium" or "aqueous environment" is one that contains at least about 50% water. Examples of aqueous media include but are not limited to water, the vitreous, extracellular fluid, conjunctiva, sclera, between the sclera and the conjunctiva, aqueous humor, gastric fluid, and any tissue or body fluid comprised of at least about 50% of water. Aqueous media include but are not limited to gel structures, including but not limited to those of the conjunctiva and sclera. In some variations described herein the liquid rapamycin formulation forms a non-dispersed mass when placed in the vitreous of a rabbit eye.

Whether a liquid formulation exhibits a non-dispersed mass relative to a surrounding medium when present in a subject or the eye of a subject may be determined by, for instance, preparing the liquid rapamycin formulation, administering it to the vitreous of a rabbit eye, and comparing the liquid formulation to the surrounding medium.

The liquid rapamycin formulations described herein may or may not form a non-dispersed mass in the subject. One liquid formulation described herein forms a non-dispersed mass when administered to a subject and forms a non-dispersed mass when administered to a rabbit eye.

It is believed that the low solubility of rapamycin in the vitreous contributes to the formation of a non-dispersed mass by some rapamycin-containing liquid formulations described herein. The vitreous is a clear gel composed almost entirely of water (up to 99%). As rapamycin in an injected formulation contacts the vitreous, the rapamycin precipitates.

Factors believed to affect the formation of and geometry of a non-dispersed mass include the concentration of rapamycin in the formulation, the viscosity of the formulation, ethanol content of the formulation, and the volume of injection. It is believed that maintaining a relatively high local concentration of rapamycin during precipitation favors formation of a non-dispersed mass. As volume is increased for a given dose, formation of a non-dispersed mass may become less favorable. Formation of a non-dispersed mass may become more favorable as rapamycin concentration is increased and/or as viscosity is increased. Ethanol content affects both the solubility of the rapamycin in the formulation and the viscosity of the formulation.

Figure 1B:
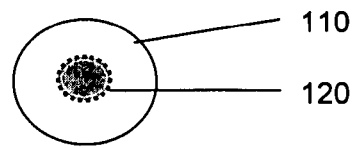
Figure 1C:
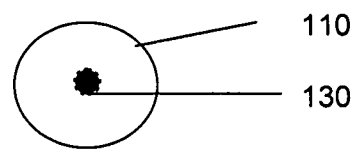

Without being bound by theory, in some variations it is hypothesized that injection of certain volumes of a liquid formulation containing rapamycin, ethanol and polyethylene glycol results in formation of a non-dispersed mass as depicted in FIGS. 1A-1C and described as follows. Upon injection, due to its viscosity a solution forms a spherical globule 100 within the vitreous 110. Ethanol then diffuses out of this globule, resulting in localized precipitation 120 of the rapamycin within the globule. Eventually, the polyethylene glycol also diffuses out of the globule to leave a solid, compact non-dispersed mass of rapamycin 130.

In some variations, upon formation a non-dispersed mass comprising rapamycin, for example, delivers the drug continuously at approximately a constant rate for an extended period of time. It is believed that delivery of rapamycin from a nor-dispersed mass in the vitreous depends on dissolution of the rapamycin in the vitreous, which depends in turn on clearance of the drug from the vitreous to other tissues. This release process is believed to maintain a steady-state concentration of rapamycin in the vitreous.

In some variations, formation of a non-dispersed mass reduces the toxicity of the injected liquid formulation compared to an equivalent dose that did not form a non-dispersed mass. In variations in which a liquid formulation injected into the vitreous does not form a non-dispersed mass, the drug appears to disperse in the vitreous body. This can interfere with vision.

In some variations, it is believed that the liquid formulations will form a visually observable non-dispersed mass when injected into the eye of a subject, including but not limited to a human subject.

In some variations, liquid formulations are believed to form non-dispersed masses when injected subconjunctivally. In some variations it is believed that when subconjunctivally administered the liquid formulation forms a depot in the scleral tissue. That is, it is believed that the therapeutic agent is absorbed into the sclera proximate to the injection site and forms a local concentration of drug in the sclera.

The compositions and liquid formulations described herein may be used to deliver amounts of rapamycin effective for treating, preventing, inhibiting, delaying on set of, or causing the regression of the diseases and conditions described herein. In some variations the compositions and liquid formulations described herein deliver one or more therapeutic agents over an extended period of time.

An "effective amount," which is also referred to herein as a "therapeutically effective amount," of rapamycin for administration as described herein is that amount of rapamycin that provides the therapeutic effect sought when administered to the subject. The achieving of different therapeutic effects may require different effective amounts of rapamycin. For example, the therapeutically effective amount of rapamycin used for preventing a disease or condition may be different from the therapeutically effective amount used for treating, inhibiting, delaying the onset of, or causing the regression of the disease or condition. In addition, the therapeutically effective amount may depend on the age, weight, and other health conditions of the subject as is well know to those versed in the disease or condition being addressed. Thus, the therapeutically effective amount may not be the same in every subject to which the rapamycin is administered.

An effective amount of rapamycin for treating, preventing, inhibiting, delaying the onset of, or causing the regression of a specific disease or condition is also referred to herein as the amount rapamycin effective to treat, prevent, inhibit, delay the onset of, or cause the regression of the disease or condition.

To determine whether a level of rapamycin is a therapeutically effective amount to treat, prevent, inhibit, delay on set of, or cause the regression of the diseases and conditions described in the Diseases and Conditions section, liquid formulations may be administered in animal models for the diseases or conditions of interest, and the effects may be observed. Dose ranging clinical trials may be performed to determine effective amounts.

The formulations described herein may further comprise various other components such as stabilizers, adjuvants, antioxidants (e.g., tocopherol, BHA, BHT, TBHQ, tocopherol acetate, ascorbyl palmitate, ascorbic acid propyl gallate, and the like), preservatives, or diluents, for example. Other components that may be used in the formulations described herein include but are not limited to agents that will (1) improve the compatibility of excipients with the encapsulating materials such as gelatin, (2) improve the stability (e.g. prevent crystal growth of a therapeutic agent such as rapamycin) of rapamycin, and/or (3) improve formulation stability. Note that there is overlap between components that are stabilizers and those that are non-aqueous liquid components, and the same component can carry out more than one role.

The rapamycin may be subjected to conventional pharmaceutical operations, such as sterilization, and compositions containing rapamycin may also contain conventional adjuvants, such as preservatives, stabilizers, wetting agents, emulsifiers, buffers etc. The liquid rapamycin formulation may also be formulated with pharmaceutically acceptable excipients for clinical use to produce a pharmaceutical composition. The liquid rapamycin formulation may be used to prepare a medicament to treat, prevent, inhibit, delay onset, or cause regression of any of the conditions described herein. In some variations, the liquid rapamycin formulation may be used to prepare a medicament to treat any of the conditions described herein.

The liquid rapamycin formulations may conveniently be presented in unit dosage form and may be prepared by conventional pharmaceutical techniques. Such techniques include the step of bringing into association the therapeutic agent and the pharmaceutical carrier(s) or excipient(s). The liquid rapamycin formulations may be prepared by uniformly and intimately bringing into associate the active ingredient with liquid carriers or finely divided solid carriers or both, and then, if necessary, shaping the product. The unit dosage form may be ready for placement or injection into the eye of a subject, or may be diluted in an aqueous or non-aqueous medium prior to injection or placement in the eye of the subject.

In some variations, the formulations described herein are provided in one or more unit dose forms, wherein the unit dose form contains an amount of a liquid rapamycin formulations described herein that is effective to treat or prevent the disease or condition for which it is being administered.

In some variations, the unit dose form is prepared in the concentration at which it will be administered. In some variations, the unit dose form is diluted prior to administration to a subject. In some variations, a liquid formulation described herein is diluted in an aqueous medium prior to administration to a subject, including but not limited to an isotonic aqueous medium. In some variations, a liquid formulation described herein is diluted in a non-aqueous medium prior to administration to a subject.

In some variations provided herein are kits comprising one or more unit dose forms as described herein. In some embodiments, the kit comprises one or more of packaging and instructions for use to treat one or more diseases or conditions. In some embodiments, the kit comprises a diluent which is not in physical contact with the formulation or pharmaceutical formulation. In some embodiments, the kit comprises any of one or more unit dose forms described herein in one or more sealed vessels. In some embodiments, the kit comprises any of one or more sterile unit dose forms.

In some variations, the unit dose form is in a container, including but not limited to a sterile sealed container. In some variations the container is a vial, ampule, or low volume applicator, including but not limited to a syringe. In some variations, a low-volume applicator is pre-filled with rapamycin for treatment of an ophthalmic disease or condition, including but not limited to a limus compound for treatment of age-related macular degeneration. Described herein is a pre-filled low-volume applicator pre-filled with a formulation comprising rapamycin. In some variations a low-volume applicator is pre-filled with a solution comprising rapamycin and a polyethylene glycol, and optionally further comprises one or more additional components including but not limited to ethanol. In some variations a low-volume applicator is pre-filled with a solution comprising about 2% rapamycin, about 94% PEG-400, about 4% ethanol.

Described herein are kits comprising one or more containers. In some variations a kit comprises one or more low-volume applicators pre-filled with one or more formulations in liquid form comprising rapamycin, including but not limited to formulations in liquid form comprising rapamycin, formulations in liquid form comprising rapamycin and a polyethylene glycol, and optionally further comprises one or more additional components including but not limited to ethanol, and formulations in liquid form comprising about 2% rapamycin, about 94% PEG-400, about 4% ethanol. In some variations the kit comprises one or more containers, including but not limited to pre-filled low-volume applicators, with instructions for its use. In a further variation a kit comprises one or more low-volume applicators pre-filled with rapamycin, with instructions for its use in treating a disease or condition of the eye.

In some variations, the containers described herein are in a secondary packaging which limits exposure of the liquid rapamycin formulation to light or oxygen.

The following references, each of which is incorporated herein by reference in its entirety, show one or more formulations, including but not limited to rapamycin formulations, and which describe use of rapamycin at various doses and other therapeutic agents for treating various diseases or conditions: U.S. 60/651,790, filed Feb. 9, 2005, titled FORMULATIONS FOR OCULAR TREATMENT, U.S. 60/664,040, filed Feb. 9, 2005, titled LIQUID FORMULATIONS FOR TREATMENT OF DISEASES OR CONDITIONS; U.S. 60/664,119, filed Mar. 21, 2005, titled DRUG DELIVERY SYSTEMS FOR TREATMENT OF DISEASES OR CONDITIONS; U.S. 60/664,306, filed Mar. 21, 2005, titled IN SITU GELLING FORMULATIONS AND LIQUID FORMULATIONS FOR TREATMENT OF DISEASES OR CONDITIONS; U.S. Pat. No. 11/351,844, filed Feb. 9, 2006, titled FORMULATIONS FOR OCULAR TREATMENT, U.S. Pat. No. 11/351,761, filed Feb. 9, 2006, titled LIQUID FORMULATIONS FOR TREATMENT OF DISEASES OR CONDITIONS; US 2005/0187241, and US 2005/0064010.

Extended Delivery of Rapamycins

Described herein are compositions and liquid formulations showing in vivo delivery or clearance profiles with one or more of the following characteristics. The delivery or clearance profiles are for clearance of rapamycin in vivo after injection of the composition or liquid formulations subconjunctivally or into the vitreous of a rabbit eye. The volume of the rabbit vitreous is approximately 30-40% of the volume of the human vitreous. Not being bound by theory, it is estimated that the surface area of the retina choroid of a rabbit eye is approximately 25% of the surface area of the retina choroid of a human eye. The amount of rapamycin is measured using techniques as described in Example 3, but without limitation to the formulation described in Example 3.

The average concentration of rapamycin in the tissue of a rabbit eye at a given time after administration of a formulation containing rapamycin may be measured according to the following method. Where volumes below 10 µl are to be injected, a Hamilton syringe is used.

The liquid formulations are stored at a temperature of 2-8° C. prior to use.

The experimental animals are specific pathogen free (SPF) New Zealand White rabbits. A mixed population of about 50% male, about 50% female is used. The rabbits are at least 12 weeks of age, usually at least 14 weeks of age, at the time of dosing. The rabbits each weigh at least 2.2 kg, usually at least 2.5 kg, at the time of dosing. Prior to the study, the animals are quarantined for at least one week and examined for general health parameters. Any unhealthy animals are not used in the study. At least 6 eyes are measured and averaged for a given timepoint.

Housing and sanitation are performed according to standard procedures used in the industry. The animals are provided approximately 150 grams of Teklad Certified Hi-Fiber Rabbit Diet daily, and are provided tap water ad libitum. No contaminants are known to exist in the water and no additional analysis outside that provided by the local water district is performed. Environmental Conditions are monitored.

Each animal undergoes a pre-treatment ophthalmic examination (slit lamp and ophthalmoscopy), performed by a board certified veterinary ophthalmologist. Ocular findings are scored according to the McDonald and Shadduck scoring system as described in Dermatoxicology, F. N. Marzulli and H. I. Maibach, 1977 "Eye Irritation," T. O. McDonald and J. A. Shadduck (pages 579-582). Observations are recorded using a standardized data collection sheet. Acceptance criteria for placement on study are as follows: scores of ≤1 for conjunctival congestion and swelling; scores of 0 for all other observation variables.

Gentamicin ophthalmic drops are placed into both eyes of each animal twice daily on the day prior to dosing, on the day of dosing (Day 1), and on the day after dosing (Day 2). Dosing is performed in two phases, the first including one set of animals and the second including the other animals. Animals are randomized separately into masked treatment groups prior to each phase of dosing according to modified Latin squares. Animals are fasted at least 8 hours prior to injection. The start time of the fast and time of injection are recorded.

Animals are weighed and anesthetized with an intravenous injection of a ketamine/xylazine cocktail (87 mg/mL ketamine, 13 mg/mL xylazine) at a volume of 0.1-0.2 mL/kg. Both eyes of each animal are prepared for injection as follows: approximately five minutes prior to injection, eyes are moistened with an ophthalmic Betadine solution. After five minutes, the Betadine is washed out of the eyes with sterile saline. Proparacairie hydrochloride 0.5% (1-2 drops) is delivered to each eye. For eyes to be intravitreally injected, 1% Tropicamide (1 drop) is delivered to each eye.

On Day 1, both eyes of each animal receive an injection of test or control article. Animals in selected groups are dosed a second time on Day 90±1. Dosing is subconjunctival or intravitreal. Actual treatments, injection locations, and dose volumes are masked and revealed at the end of the study.

Subconjunctival injections are given using an insulin syringe and 30 gauge×½-inch needle. The bulbar conjunctiva in the dorsotemporal quadrant is elevated using forceps. Test article is injected into the subconjunctival space.

Intravitreal injections are given using an Insulin syringe and 30 gauge×½-inch needle. For each injection, the needle is introduced through the ventral-nasal quadrant of the eye, approximately 2-3 mm posterior to the limbus, with the bevel of the needle directed downward and posteriorly to avoid the lens. Test article is injected in a single bolus in the vitreous near the retina.

Animals are observed for mortality/morbidity twice daily. An animal determined to be moribund is euthanized with an intravenous injection of commercial euthanasia solution. Both eyes are removed and stored frozen at −70° C. for possible future evaluation. If an animal is found dead prior to onset of rigor mortis, both eyes are removed and stored frozen at −70° C. for possible future evaluation. Animals found after the onset of rigor mortis are not necropsied.

Animals are weighed at randomization, on Day 1 prior to dosing, and prior to euthanasia.

Ophthalmic observations (slit lamp and indirect ophthalmoscopy) are performed on all animals on Days 5±1, 30±1, 60±1, 90±1, and at later dates in some variations. Observations are performed by a board certified veterinary ophthalmologist. For animals to be dosed on Day 90±1, ophthalmic observations are performed prior to dosing. Ocular findings are scored according to the McDonald and Shadduck scoring system as described in Dermatoxicology, F. N. Marzulli and H. I. Maibach, 1977 "Irritation", T. O. McDonald and J. A. Shadduck (pages 579-582) and observations are recorded using a standardized data collection sheet.

Whole blood samples (1-3 mL per sample) are collected from each animal prior to necropsy in vacutainer tubes containing EDTA. Each tube is filled at least ⅔ full and thoroughly mixed for at least 30 seconds. Tubes are stored frozen until shipped on dry ice.

Animals are euthanized with an intravenous injection of commercial euthanasia solution. Euthanasia is performed according to standard procedures used in the industry.

For treatment groups dosed intravitreally or subconjunctivally with placebo, all eyes from each of these groups are placed into Davidsons solution for approximately 24 hours. Following the 24-hour period, the eyes are transferred to 70% ethanol; these globes are submitted for masked histopathological evaluation by a board certified veterinary pathologist. The time that eyes are placed into Davidsons and the time of removal are recorded.

For treatment groups dosed intravitreally or subconjunctivally with test article, some eyes from each of these groups are frozen at −70° C. and submitted for pharmacokinetic analysis. The remaining eyes from each of these groups are placed into Davidsons solution for approximately 24 hours. Following the 24-hour period, the eyes are transferred to 70% ethanol; these globes are submitted for masked histopathological evaluation by a board certified veterinary pathologist. The time that eyes are placed into Davidsons and the time of removal are recorded.

Frozen samples submitted for pharmacokinetic analysis are dissected with disposable instruments. One set of instruments is used per eye, and then discarded. The samples are thawed at room temperature for 1 to 2 minutes to ensure that the frost around the tissue has been removed. The sclera is dissected into 4 quadrants, and the vitreous is removed. If a non-dispersed mass (NDM) is clearly visible within the vitreous, the vitreous is separated into two sections. The section with the NDM is approximately two-thirds of the vitreous. The section without the NDM is the portion of the vitreous that is the most distant from the NDM. The aqueous humor, lens, iris, and cornea are separated. The retina choroid tissue is removed using a forceps and collected for analysis. The conjunctiva is separated from the sclera.

The various tissue types are collected into separate individual pre-weighed vials which are then capped and weighed. The vials of tissue are stored at −80° C. until analyzed.

The sirolimus content of the retina choroid, sclera, vitreous humor, and whole anti-coagulated blood is determined by high-pressure liquid chromatography/tandem mass spectroscopy (HPLC/MS/MS) using 32-O-desmethoxyrapamycin as an internal standard. Where an NDM was observed in the vitreous, the section of the vitreous containing the NDM and the section of the vitreous not containing the NDM are analyzed separately.

The average concentration of rapamycin over a period of time means for representative timepoints over the period of time the average concentration at each time point. For example, if the time period is 30 days, the average concentration may be measured at 5 day intervals: for the average concentration at day 5, the average of a number of measurements of concentration at day 5 would be calculated; for the average concentration at day 10, the average of a number of measurements of the concentration at day 10 would be calculated, etc.

Figure 2:
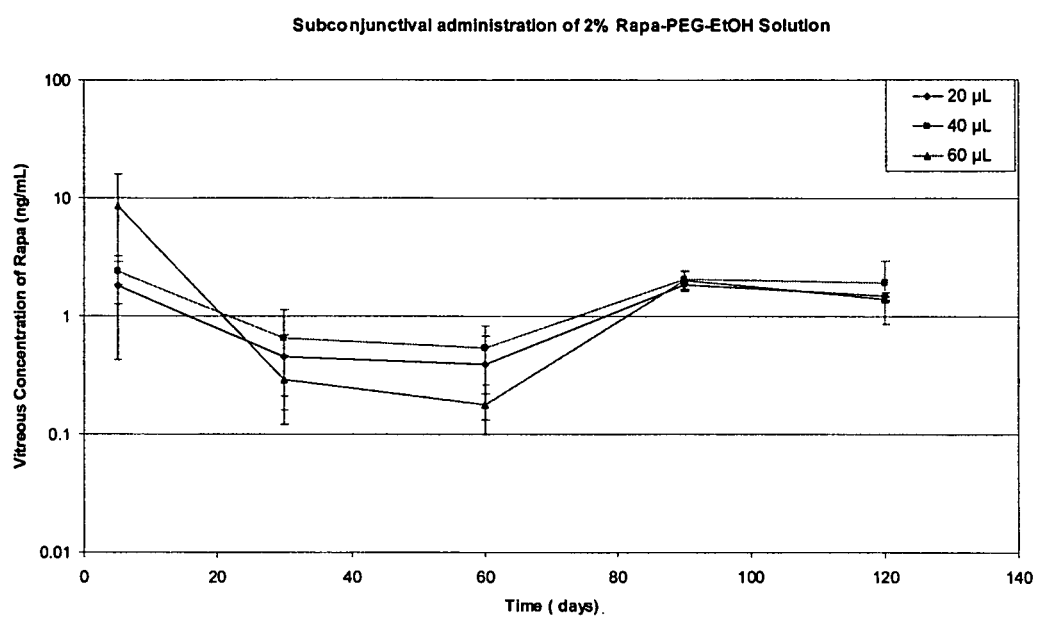
FIG. 2 depicts the level of rapamycin in the vitreous of rabbit eyes (ng/ml) at 5, 30, 60, 90, and 120 days after subconjunctival injection of 20 µl, 40 µl, and 60 µl doses of a 2% solution of rapamycin in ethanol and PEG 400.

In some variations, the liquid formulations described herein may have in vivo delivery to the vitreous profiles with the following described characteristics, where the delivery profiles are for delivery of rapamycin in vivo after injection of the liquid formulation between the sclera and the conjunctiva of a rabbit eye. One nonlimiting variation of in vivo delivery to the vitreous profiles is shown in FIG. 2.

"Approximately constant," as used herein, means that the average level does not vary by more than one order of magnitude over the extended period of time, i.e., the difference between the maximum and minimum is less than a 10-fold difference for measurements of the average concentration at times in the relevant period of time.

In some variations, the liquid rapamycin formulation when injected between the sclera and conjunctiva of a rabbit eye delivers rapamycin giving an average concentration of rapamycin in the vitreous of the rabbit eye of at least 0.001 ng/mL for at least 30, at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving an average concentration of rapamycin in the vitreous of the rabbit eye of at least 0.01 ng/mL for at least 30, at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving an average concentration of rapamycin in the vitreous of the rabbit eye of at least 0.1 ng/mL for at least 30, at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving an average concentration of rapamycin in the vitreous of the rabbit eye of at least 0.5 ng/mL for at least 30, at least 60, at least 90, or at least 120 days after administration of the liquid rapamycin formulation to the rabbit eyes.

In some variations, the liquid rapamycin formulation when injected between the sclera and conjunctiva of a rabbit eye delivers rapamycin giving an average concentration of rapamycin in the vitreous of the rabbit eye of between 0.001 ng/mL and 10.0 ng/mL for at least 30, at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving an average concentration of rapamycin in the vitreous of the rabbit eye of between 0.01 ng/mL and 10 ng/mL for at least 30, at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving an average concentration of rapamycin in the vitreous of the rabbit eye of between 0.1 ng/mL and 10 ng/mL for at least 30, at least 60, at least 90, or at least 120 days after administration of the liquid rapamycin formulation to the rabbit eyes.

In some variations, the liquid rapamycin formulation when injected between the sclera and conjunctiva of a rabbit eye delivers rapamycin giving an average concentration of rapamycin in the vitreous of the rabbit eye of between 0.5 ng/mL and 10.0 ng/mL for at least 30, at least 60, at least 90, or at least 120 days after administration of the liquid rapamycin formulation to the rabbit eyes.

In some variations, the liquid rapamycin formulation when injected between the sclera and conjunctiva of a rabbit eye delivers rapamycin giving a ratio of a maximum average concentration of rapamycin in the vitreous of a rabbit eye to a minimum average concentration of rapamycin in the vitreous of a rabbit eye less than 100 for days 30 to at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving a ratio of a maximum average concentration of rapamycin in the vitreous of a rabbit eye to a minimum average concentration of rapamycin in the vitreous of a rabbit eye less than 50 for days 30 to at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving a ratio of a maximum average concentration of rapamycin in the vitreous of a rabbit eye to a minimum average concentration of rapamycin in the vitreous of a rabbit eye less than 10 for days 30 to at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving a ratio of a maximum average concentration of rapamycin in the vitreous of a rabbit eye to a minimum average concentration of rapamycin in the vitreous of a rabbit eye less than 5 for days 30 to at least 60, at least 90, or at least 120 days after administration of the liquid rapamycin formulation to the rabbit eyes.

In some variations, the liquid rapamycin formulation when injected between the sclera and conjunctiva of a rabbit eye delivers rapamycin giving an average concentration of rapamycin in the vitreous of a rabbit eye that is approximately constant at a value greater than 0.001 ng/mL for days 30 to at least 60, at least 90, or at least 120 days after administration of the solution to the rabbit eyes. In some variations, the liquid rapamycin formulation when injected between the sclera and conjunctiva of a rabbit eye delivers rapamycin giving an average concentration of rapamycin in the vitreous of a rabbit eye that is approximately constant at a value greater than 0.01 ng/mL for days 30 to at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving an average concentration of rapamycin in the vitreous of a rabbit eye that is approximately constant at a value greater than 0.1 ng/mL for days 30 to at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving an average concentration of rapamycin in the vitreous of a rabbit eye that is approximately constant at a value of 1.0 ng/mL for days 30 to at least 60, at least 90, or at least 120 days after administration of the liquid rapamycin formulation to the rabbit eyes.

In some variations, the liquid rapamycin formulation when injected between the sclera and conjunctiva of a rabbit eye delivers rapamycin giving an average concentration of rapamycin in the retina choroid tissues of the rabbit eye of at least 0.001 ng/mg for at least 30, at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving an average concentration of rapamycin in the retina choroid tissues of the rabbit eye of at least 0.005 ng/mg for at least 30, at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving an average concentration of rapamycin in the retina choroid tissues of the rabbit eye of at least 0.01 ng/mg for at least 30, at least 60, at least 90, or at least 120 days after administration of the liquid rapamycin formulation to the rabbit eyes.

In some variations, the liquid rapamycin formulation when injected between the sclera and conjunctiva of a rabbit eye delivers rapamycin giving an average concentration of rapamycin in the retina choroid tissues of the rabbit eye of between 0.001 ng/mg and 1.0 ng/mg for at least 30, at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving an average concentration of rapamycin in the retina choroid tissues of the rabbit eye of between 0.001 ng/mg and 0.50 ng/mg for at least 30, at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving an average concentration of rapamycin in the retina choroid tissues of the rabbit eye of between 0.001 ng/mg and 0.15 ng/mg for at least 30, at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving an average concentration of rapamycin in the retina choroid tissues of the rabbit eye of between 0.001 ng/mg and 0.1 ng/mg for at least 30, at least 60, at least 90, or at least 120 days after administration of the liquid rapamycin formulation to the rabbit eyes.

In some variations, the liquid rapamycin formulation when injected between the sclera and conjunctiva of a rabbit eye delivers rapamycin giving an average concentration of rapamycin in the retina choroid tissues of the rabbit eye of between 0.005 ng/mg and 1.0 ng/mg for at least 30, at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving an average concentration of rapamycin in the retina choroid tissues of the rabbit eye of between 0.005 ng/mg and 0.50 ng/mg for at least 30, at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving an average concentration of rapamycin in the retina choroid tissues of the rabbit eye of between 0.005 ng/mg and 0.15 ng/mg for at least 30, at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving an average concentration of rapamycin in the retina choroid tissues of the rabbit eye of between 0.005 ng/mg and 0.1 ng/mg for at least 30, at least 60, at least 90, or at least 120 days after administration of the liquid rapamycin formulation to the rabbit eyes.

In some variations, the liquid rapamycin formulation when injected between the sclera and conjunctiva of a rabbit eye delivers rapamycin giving an average concentration of rapamycin in the retina choroid tissues of the rabbit eye of between 0.01 ng/mg and 1.0 ng/mg for at least 30, at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving an average concentration of rapamycin in the retina choroid tissues of the rabbit eye of between 0.01 ng/mg and 0.50 ng/mg for at least 30, at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving an average concentration of rapamycin in the retina choroid tissues of the rabbit eye of between 0.01 ng/mg and 0.15 ng/mg for at least 30, at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving an average concentration of rapamycin in the retina choroid tissues of the rabbit eye of between 0.01 ng/mg and 0.1 ng/mg for at least 30, at least 60, at least 90, or at least 120 days after administration of the liquid rapamycin formulation to the rabbit eyes.

In some variations, the liquid rapamycin formulation when injected between the sclera and conjunctiva of a rabbit eye delivers rapamycin giving a ratio of a maximum average concentration of rapamycin in the retina choroid tissues of a rabbit eye to a minimum average concentration of rapamycin in the retina choroid tissues of a rabbit eye less than 100 for days 30 to at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving a ratio of a maximum average concentration of rapamycin in the retina choroid tissues of a rabbit eye to a minimum average concentration of rapamycin in the retina choroid tissues of a rabbit eye less than 50 for days 30 to at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving a ratio of a maximum average concentration of rapamycin in the retina choroid tissues of a rabbit eye to a minimum average concentration of rapamycin in the retina choroid tissues of a rabbit eye less than 10 for days 30 to at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving a ratio of a maximum average concentration of rapamycin in the retina choroid tissues of a rabbit eye to a minimum average concentration of rapamycin in the retina choroid tissues of a rabbit eye less than 5 for days 30 to at least 60, at least 90, or at least 120 days after administration of the liquid rapamycin formulation to the rabbit eyes.

In some variations, the liquid rapamycin formulation when injected between the sclera and conjunctiva of a rabbit eye delivers rapamycin giving an average concentration of rapamycin in the retina choroid tissues of a rabbit eye that is approximately constant at a value greater than 0.001 ng/mg for days 30 to at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving an average concentration of rapamycin in the retina choroid tissues of a rabbit eye that is approximately constant at a value greater than 0.005 ng/mg for days 30 to at least 60, at least 90, or at least 120 days after administration of the liquid rapamycin formulation to the rabbit eyes. In some variations, the liquid rapamycin formulation when injected between the sclera and conjunctiva of a rabbit eye delivers rapamycin giving an average concentration of rapamycin in the retina choroid tissues of a rabbit eye that is approximately constant at a value greater than 0.01 ng/mg for days 30 to at least 60, at least 90, or at least 120 days after administration of the liquid rapamycin formulation to the rabbit eyes.

In some variations, the liquid rapamycin formulation when injected into the vitreous of a rabbit eye delivers rapamycin giving an average concentration of rapamycin in the vitreous of the rabbit eye of at least 100 ng/mL for at least 30, at least 60, at least 90, or at least 120 days after administration of the liquid rapamycin formulation to the rabbit eyes. In some variations, the liquid rapamycin formulation when injected into the vitreous of a rabbit eye delivers rapamycin giving an average concentration of rapamycin in the vitreous of the rabbit eye of at least 1000 ng/mL for at least 30, at least 60, at least 90, or at least 120 days after administration of the liquid rapamycin formulation to the rabbit eyes. In some variations, the liquid rapamycin formulation when injected into the vitreous of a rabbit eye delivers rapamycin giving an average concentration of rapamycin in the vitreous of the rabbit eye of at least 10,000 ng/mL for at least 30, at least 60, at least 90, or at least 120 days after administration of the liquid rapamycin formulation to the rabbit eyes.

In some variations, the liquid rapamycin formulation when injected into the vitreous of a rabbit eye delivers rapamycin giving an average concentration of rapamycin in the vitreous of the rabbit eye between 100 ng/mL and 100,000 ng/mL for day 30 to at least 60, at least 90, or at least 120 days after administration of the liquid rapamycin formulation to the rabbit eyes. In some variations, the liquid rapamycin formulation when injected into the vitreous of a rabbit eye delivers rapamycin giving an average concentration of rapamycin in the vitreous of the rabbit eye between 100 ng/mL and 50,000 ng/mL for day 30 to at least 60, at least 90, or at least 120 days after administration of the liquid rapamycin formulation to the rabbit eyes.

In some variations, the liquid rapamycin formulation when injected into the vitreous of a rabbit eye delivers rapamycin giving an average concentration of rapamycin in the vitreous of the rabbit eye between 1000 ng/mL and 100,000 ng/mL for day 30 to at least 60, at least 90, or at least 120 days after administration of the liquid rapamycin formulation to the rabbit eyes. In some variations, the liquid rapamycin formulation when injected into the vitreous of a rabbit eye delivers rapamycin giving an average concentration of rapamycin in the vitreous of the rabbit eye between 1000 ng/mL and 50,000 ng/mL for day 30 to at least 60, at least 90, or at least 120 days after administration of the liquid rapamycin formulation to the rabbit eyes.

In some variations, the liquid rapamycin formulation when injected into the vitreous of a rabbit eye delivers rapamycin giving a ratio of a maximum average concentration of rapamycin in the vitreous of the rabbit eye to a minimum average concentration of rapamycin in the vitreous of the rabbit eye less than 100 for days 30 to at least 60, at least 90, or at least 120 days after administration of the liquid rapamycin formulation to the rabbit eyes. In some variations, the liquid rapamycin formulation when injected into the vitreous of a rabbit eye delivers rapamycin giving a ratio of a maximum average concentration of rapamycin in the vitreous of the rabbit eye to a minimum average concentration of rapamycin in the vitreous of the rabbit eye less than 50 for days 30 to at least 60, at least 90, or at least 120 days after administration of the liquid rapamycin formulation to the rabbit eyes. In some variations, the liquid rapamycin formulation when injected into the vitreous of a rabbit eye delivers rapamycin giving a ratio of a maximum average concentration of rapamycin in the vitreous of the rabbit eye to a minimum average concentration of rapamycin in the vitreous of the rabbit eye less than 10 for days 30 to at least 60, at least 90, or at least 120 days after administration of the liquid rapamycin formulation to the rabbit eyes.

In some variations, the liquid rapamycin formulation when injected into the vitreous of a rabbit eye delivers rapamycin giving an average concentration of rapamycin in the vitreous of the rabbit eye that is approximately constant at a value greater than 100 ng/mL for days 30 to at least 60, at least 90, or at least 120 days after administration of the liquid rapamycin formulation to the rabbit eyes. In some variations, the liquid rapamycin formulation when injected into the vitreous of a rabbit eye delivers rapamycin giving an average concentration of rapamycin in the vitreous of the rabbit eye that is approximately constant at a value greater than 1000 ng/mL for days 30 to at least 60, at least 90, or at least 120 days after administration of the liquid rapamycin formulation to the rabbit eyes. In some variations, the liquid rapamycin formulation when injected into the vitreous of a rabbit eye delivers rapamycin giving an average concentration of rapamycin in the vitreous of the rabbit eye that is approximately constant at a value greater than 10,000 ng/mL for days 30 to at least 60, at least 90, or at least 120 days after administration of the liquid rapamycin formulation to the rabbit eyes.

In some variations, the liquid rapamycin formulation when injected into the vitreous of a rabbit eye delivers rapamycin giving an average concentration of rapamycin in the retina choroid tissues of the rabbit eye of at least 0.001 ng/mg for at least 30, at least 60, at least 90, or at least 120 days after administration of the liquid rapamycin formulation to the rabbit eyes. In some variations, the liquid rapamycin formulation when injected into the vitreous of a rabbit eye delivers rapamycin giving an average concentration of rapamycin in the retina choroid tissues of the rabbit eye of at least 0.01 ng/mg for at least 30, at least 60, at least 90, or at least 120 days after administration of the liquid rapamycin formulation to the rabbit eyes. In some variations, the liquid rapamycin formulation when injected into the vitreous of a rabbit eye delivers rapamycin giving an average concentration of rapamycin in the retina choroid tissues of the rabbit eye of at least 0.05 ng/mg for at least 30, at least 60, at least 90, or at least 120 days after administration of the liquid rapamycin formulation to the rabbit eyes. In some variations, the liquid rapamycin formulation when injected into the vitreous of a rabbit eye delivers rapamycin giving an average concentration of rapamycin in the retina choroid tissues of the rabbit eye of at least 0.10 ng/mg for at least 30, at least 60, at least 90, or at least 120 days after administration of the liquid rapamycin formulation to the rabbit eyes.

In some variations, the liquid rapamycin formulation when injected into the vitreous of a rabbit eye delivers rapamycin giving an average concentration of rapamycin in the retina choroid tissues of the rabbit eye between 0.001 ng/mg and 10.00 ng/mg for at least 30, at least 60, at least 90, or at least 120 days after administration of the liquid rapamycin formulation to the rabbit eyes. In some variations, the liquid rapamycin formulation when injected into the vitreous of a rabbit eye delivers rapamycin giving an average concentration of rapamycin in the retina choroid tissues of the rabbit eye between 0.001 ng/mg and 5.00 ng/mg for at least 30, at least 60, at least 90, or at least 120 days after administration of the liquid rapamycin formulation to the rabbit eyes. In some variations, the liquid rapamycin formulation when injected into the vitreous of a rabbit eye delivers rapamycin giving an average concentration of rapamycin in the retina choroid tissues of the rabbit eye between 0.001 ng/mg and 1.00 ng/mg for at least 30, at least 60, at least, 90, or at least 120 days after administration of the liquid rapamycin formulation to the rabbit eyes.

In some variations, the liquid rapamycin formulation when injected into the vitreous of a rabbit eye delivers rapamycin giving an average concentration of rapamycin in the retina choroid tissues of the rabbit eye between 0.01 ng/mg and 10.00 ng/mg for at least 30, at least 60, at least 90, or at least 120 days after administration of the liquid rapamycin formulation to the rabbit eyes. In some variations, the liquid rapamycin formulation when injected into the vitreous of a rabbit eye delivers rapamycin giving an average concentration of rapamycin in the retina choroid tissues of the rabbit eye between 0.01 ng/mg and 5.00 ng/mg for at least 30, at least 60, at least 90, or at least 120 days after administration of the liquid rapamycin formulation to the rabbit eyes. In some variations, the liquid rapamycin formulation when injected into the vitreous of a rabbit eye delivers rapamycin giving an average concentration of rapamycin in the retina choroid tissues of the rabbit eye between 0.01 ng/mg and 1.00 ng/mg for at least 30, at least 60, at least 90, or at least 120 days after administration of the liquid rapamycin formulation to the rabbit eyes.

In some variations, the liquid rapamycin formulation when injected into the vitreous of a rabbit eye delivers rapamycin giving an average concentration of rapamycin in the retina choroid tissues of the rabbit eye between 0.05 ng/mg and 10.00 ng/mg for at least 30, at least 60, at least 90, or at least 120 days after administration of the liquid rapamycin formulation to the rabbit eyes. In some variations, the liquid rapamycin formulation when injected into the vitreous of a rabbit eye delivers rapamycin giving an average concentration of rapamycin in the retina choroid tissues of the rabbit eye between 0.05 ng/mg and 5.00 ng/mg for at least 30, at least 60, at least 90, or at least 120 days after administration of the liquid rapamycin formulation to the rabbit eyes. In some variations, the liquid rapamycin formulation when injected into the vitreous of a rabbit eye delivers rapamycin giving an average concentration of rapamycin in the retina choroid tissues of the rabbit eye between 0.05 ng/mg and 1.00 ng/mg for at least 30, at least 60, at least 90, or at least 120 days after administration of the liquid rapamycin formulation to the rabbit eyes.

In some variations, the liquid rapamycin formulation when injected into the vitreous of a rabbit eye delivers rapamycin giving an average concentration of rapamycin in the retina choroid tissues of the rabbit eye between 0.10 ng/mg and 10.00 ng/mg for at least 30, at least 60, at least 90, or at least 120 days after administration of the liquid rapamycin formulation to the rabbit eyes. In some variations, the liquid rapamycin formulation when injected into the vitreous of a rabbit eye delivers rapamycin giving an average concentration of rapamycin in the retina choroid tissues of the rabbit eye between 0.10 ng/mg and 5.00 ng/mg for at least 30, at least 60, at least 90, or at least 120 days after administration of the liquid rapamycin formulation to the rabbit eyes. In some variations, the liquid rapamycin formulation when injected into the vitreous of a rabbit eye delivers rapamycin giving an average concentration of rapamycin in the retina choroid tissues of the rabbit eye between 0.10 ng/mg and 1.00 ng/mg for at least 30, at least 60, at least 90, or at least 120 days after administration of the liquid rapamycin formulation to the rabbit eyes.

In some variations, the liquid rapamycin formulation when injected into the vitreous of a rabbit eye delivers rapamycin giving a ratio of a maximum average concentration of rapamycin in the retina choroid tissues of the rabbit eye to a minimum average concentration of rapamycin in the retina choroid tissues of the rabbit eye less than 100 for days 30 to at least 60, at least 90, or at least 120 days after administration of the liquid rapamycin formulation to the rabbit eyes. In some variations, the liquid rapamycin formulation when injected into the vitreous of a rabbit eye delivers rapamycin giving a ratio of a maximum average concentration of rapamycin in the retina choroid tissues of the rabbit eye to a minimum average concentration of rapamycin in the retina choroid tissues of the rabbit eye less than 50 for days 30 to at least 60, at least 90, or at least 120 days after administration of the liquid rapamycin formulation to the rabbit eyes.

In some variations, the ratio of the base ten logarithms of the average levels of rapamycin in the vitreous and the retina choroid tissues is approximately constant over an extended period of time. Put another way, as the level of rapamycin in the vitreous rises, the level of rapamycin in the retina choroid tissues rises to a similar degree when considered on the logarithmic scale, and vice versa.

In some variations, the ratio of the base ten logarithms of the average levels of rapamycin in the vitreous versus the retina choroid tissues is approximately constant over an extended period of time of 7, 30, 60, or 90 days.

For treatment, prevention, inhibition, delaying the onset of, or causing the regression of certain diseases or conditions, it may be desirable to maintain delivery of a therapeutically effective amount of rapamycin for an extended period of time. Depending on the disease or condition being treated, prevented, inhibited, having onset delayed, or being caused to regress this extended period of time may be at least about 1 week, at least about 2 weeks, at least about 3 weeks, at least about 1 month, at least about 3 months, at least about 6 months, at least about 9 months, or at least about 1 year. Generally, however, any extended period of delivery may be possible. A therapeutically effective amount of agent may be delivered for an extended period by a liquid formulation or composition that maintains for the extended period a concentration of agent in a subject or an eye of a subject sufficient to deliver a therapeutically effective amount of agent for the extended time.

Delivery of a therapeutically effective amount of rapamycin for an extended period may be achieved via a single administration of a liquid rapamycin formulation or may be achieved by administration of two or more doses of a liquid rapamycin formulation. As a non-limiting example of such multiple applications, maintenance of the therapeutic amount of rapamycin for 3 months for treatment, prevention, inhibition, delay of onset, or cause of regression of wet AMD may be achieved by administration of one dose of a liquid rapamycin formulation delivering a therapeutic amount for 3 months or by sequential application of a plurality of doses of a liquid rapamycin formulation. The optimal dosage regime will depend on the therapeutic amount of rapamycin needing to be delivered, the period over which it need be delivered, and the delivery kinetics of the liquid formulation. Those versed in such extended therapeutic agent delivery dosing will understand how to identify dosing regimes that may be used based on the teachings described herein.

When using rapamycin for the treatment, prevention, inhibition, delaying the onset of, or causing the regression of certain diseases, it may be desirable for delivery of the rapamycin not to commence immediately upon placement of the liquid formulation or composition into the eye region, but for delivery to commence after some delay. For example, but in no way limiting, such delayed release may be useful where the rapamycin inhibits or delays wound healing and delayed release is desirable to allow healing of any wounds occurring upon placement of the liquid formulation or composition. Depending on the therapeutic agent being delivered and/or the diseases and conditions being treated, prevented, inhibited, onset delayed, and regression caused this period of delay before delivery of rapamycin commences may be about: 1 hour, about 6 hours, about 12 hours, about 18 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 21 days, about 28 days, about 35 days, or about 42 days. Other delay periods may be possible. Delayed release formulations that may be used are known to people versed in the technology.

Routes of Administration

"Retina choroid" and "retina choroid tissues," as used herein, are synonymous and refer to the combined retina and choroid tissues of the eye.

"Subconjunctival" placement or injection, as used herein, refers to placement or injection, respectively, between the sclera and conjunctiva. Subconjunctival is sometimes referred to herein as "sub-conj" administration.

By way of nonlimiting example, the liquid rapamycin formulation described herein may be administered to the vitreous, aqueous humor, sclera, conjunctiva, between the sclera and conjunctiva, the retina choroid tissues, macula, or other area in or proximate to the eye of a human subject, in amounts and for a duration effective to treat, prevent, inhibit, delay the onset of, or cause the regression of CNV and wet AMD.

Periocular routes of delivery may deliver rapamycin to the retina without some of the risks of intravitreal delivery. Periocular routes include but are not limited to subconjunctival, subtenon, retrobulbar, peribulbar and posterior juxtascleral delivery. A "periocular" route of administration means placement near or around the eye. For a description of exemplary periocular routes for retinal drug delivery, see *Periocular routes for retinal drug delivery*, Raghava et al. (2004), Expert Opin. Drug Deliv. 1(1):99-114, which is incorporated herein by reference in its entirety.

In some variations the liquid formulations described herein are administered intraocularly. Intraocular administration includes placement or injection within the eye, including in the vitreous.

In some variations, an effective amount of rapamycin is placed intravitreally or subconjunctivally to treat, prevent, inhibit, delay the onset of, or cause the regression of CNV, wet AMD, or dry AMD.

Intravitreal administration is more invasive than some other types of ocular procedures. Because of the potential risks of adverse effects, intravitreal administration may not be optimal for treatment of relatively healthy eyes. By contrast, periocular administration, such as subconjunctival administration, is much less invasive than intravitreal administration. When rapamycin is delivered by a periocular route, it may be possible to treat patients with healthier eyes than could be treated using intravitreal administration. In some variations, subconjunctival injection is used to prevent or delay onset of a disease or condition of the eye, where the eye of the subject has visual acuity of 20/40 or better.

Routes of administration that may be used to administer a liquid formulation include but are not limited to placement of the liquid formulation, for example by injection, into an aqueous medium in the subject, including but not limited to subconjunctival and intravitreal placement, including but not limited to injection.

Compositions and liquid formulations comprising rapamycin can be administered directly to the eye using a variety of procedures, including but not limited to procedures in which (1) rapamycin is administered by injection, including but not limited to administration by using a syringe and hypodermic needle, an insulin needle, or a Hamilton HPLC-type needle, or (2) a specially designed device is used to inject rapamycin.

Intravitreal and Subconjunctival Delivery of Rapamycin for Treatment, Prevention, Inhibition, Delay of Onset, or Cause of Regression of AMD As used herein, to "prevent" a disease or condition by administration of rapamycin means that the detectable physical characteristics or symptom of the disease or condition do not develop following administration of rapamycin.

As used herein, to "delay onset of" a disease or condition by administration of rapamycin means that at least one detectable physical characteristic or symptom of the disease or condition develops later in time following administration of rapamycin as compared to the progress of the disease or condition without administration of rapamycin.

As used herein, to "treat" a disease or condition by administration of rapamycin means that the progress of at least one detectable physical characteristic or symptom of the disease or condition is slowed, stopped, or reversed following administration of rapamycin as compared to the progress of the disease or condition without administration of rapamycin.

A subject having a predisposition for or in need of prevention may be identified by the skilled practitioner by established methods and criteria in the field given the teachings herein. The skilled practitioner may also readily diagnose individuals as in need of inhibition or treatment based upon established criteria in the field for identifying angiogenesis and/or neovascularization given the teachings herein.

As used herein, a "subject" is generally any animal that may benefit from administration of rapamycin as described herein. The rapamycin may be administered to a mammal subject. Unless the context appears otherwise, all of the methods described herein may be performed on a human subject. The rapamycin may be administered to a veterinary animal subject. The rapamycin may be administered to a model experimental animal subject.

In some variations described herein, a solution comprising rapamycin is delivered subconjunctivally or to the vitreous of an eye of a subject, including but not limited to a human subject, to prevent, treat, inhibit, delay onset of, or cause regression of angiogenesis in the eye, including but not limited to treating CNV as observed, for example, in AMD. In some variations, the solution is used to treat angiogenesis in the eye, including but not limited to treating CNV as observed, for example, in AMD. Rapamycin has been shown to inhibit CNV in rat and mice models, as described in U.S. application Ser. No. 10/665,203, which is incorporated herein by reference in its entirety. Rapamycin has been observed to inhibit Matrigel™ and laser-induced CNV when administered systemically and subretinally.

In some variations, the formulations and pharmaceutical formulations described herein are used to prevent or delay onset of a disease or condition of the eye where the subject, including but not limited to a human subject, is at heightened risk of developing the disease or condition of the eye. A subject with a heightened risk of developing a disease or condition is a subject with one or more indications that the disease or condition is likely to develop in the particular subject. In some variations the subject with a heightened risk of developing wet AMD is a subject with dry AMD in at least one eye. In some variations the subject with a heightened risk of developing wet AMD in a fellow eye is a subject with wet AMD in the other eye. In some variations, the formulations and pharmaceutical formulations described herein are used to prevent or delay onset of CNV in a subject at heightened risk of developing CNV, including but not limited to prevention or delaying onset of CNV in the fellow eye of a subject, including but not limited to a human subject with AMD in one eye. In some variations, the formulations and pharmaceutical formulations described herein are used to prevent or delay onset of CNV in the fellow eye of a subject with wet AMD in one eye. In some variations, the formulations and pharmaceutical formulations comprise a limus compound, including but not limited to rapamycin. In some variations the formulations and pharmaceutical formulations are administered subconjunctivally to an eye with vision of 20/40 or better.

As described herein, the dosage of rapamycin will depend on the condition being addressed, whether the condition is to be treated, prevented, inhibited, have onset delayed, or be caused to regress, the particular therapeutic agent, and other clinical factors such as weight and condition of the subject and the route of administration of the therapeutic agent. It is to be understood that the methods, liquid formulations, and compositions described herein have application for both human and veterinary use, as well as uses in other possible animals. As described herein, tissue concentrations of rapamycin expressed in units of mass per volume generally refer to tissues that are primarily aqueous such as the vitreous, for example. Tissue concentrations of rapamycin expressed in unit of mass per mass generally refer to other tissues such as the sclera or retina choroid tissues, for example.

The liquid rapamycin formulations described herein may deliver rapamycin for an extended period of time. One non-limiting example of such an extended release delivery system is a liquid rapamycin formulation that delivers rapamycin to a subject or to the eye of a subject in an amount sufficient to treat, prevent, inhibit, delay onset of, or cause regression of wet age-related macular degeneration for an extended period of time. In some variations, the liquid formulation is used to treat wet age-related macular degeneration for an extended period of time. In some variations, the liquid formulation is used to prevent wet age-related macular degeneration for an extended period of time. In some variations, the liquid formulation is used to prevent transition of dry AMD to wet AMD for an extended period of time.

One concentration of rapamycin that may be used in the methods described herein is one that provides to a subject about 0.01 pg/ml or pg/mg or more of rapamycin at the tissue level. Another concentration that may be used is one that provides to a subject about 0.1 pg/ml or ng/mg or more at the tissue level. Another concentration that may be used is one that provides to a subject about 1 pg/ml or ng/mg or more at the tissue level. Another concentration that may be used is one that provides to a subject about 0.01 ng/ml or ng/mg or more at the tissue level. Another concentration that may be used is one that provides to a subject about 0.1 ng/ml or ng/mg or more at the tissue level. Another concentration that may be used is one that provides to a subject about 0.5 ng/ml or ng/mg or more at the tissue level. Another concentration that may be used is one that provides to a subject about 1 ng/ml or more at the tissue level. Another concentration that may be used is one that provides to a subject about 2 ng/ml or more at the tissue level. Another concentration that may be used is one that provides to a subject about 3 ng/ml or more at the tissue level. Another concentration that may be used is one that provides to a subject about 5 ng/ml or more at the tissue level. Another concentration that may be used is one that provides to a subject about 10 ng/ml or more at the tissue level. Another concentration that may be used is one that provides to a subject about 15 ng/ml or more at the tissue level. Another concentration that may be used is one that provides to a subject about 20 ng/ml or more at the tissue level. Another concentration that may be used is one that provides to a subject about 30 ng/ml or more at the tissue level. Another concentration that may be used is one that provides to a subject about 50 ng/ml or more at the tissue level. One of ordinary skill in the art would know how to arrive at an appropriate concentration depending on the route and duration of administration utilized, given the teachings herein.

Generally, the amount of rapamycin administered in a liquid formulation is an amount sufficient to treat, prevent, inhibit, delay the onset, or cause regression of the disease or condition of the eye for the required amount of time. In some variations the amount of rapamycin administered in the liquid formulation is an amount sufficient to treat the disease or condition of the eye for the required amount of time.

In some variations, a total amount of rapamycin less than about 5 mg is administered subconjunctivally. In some variations, a total amount of rapamycin less than about 5.0 mg is administered subconjunctivally. In some variations, a total amount of rapamycin less than about 4.5 mg is administered subconjunctivally. In some variations, a total amount of rapamycin less than about 4.0 mg is administered subconjunctivally. In some variations, a total amount of rapamycin less than about 3.5 mg is administered subconjunctivally. In some variations, a total amount of rapamycin less than about 3.0 mg is administered subconjunctivally. In some variations, a total amount of rapamycin less than about 2.5 mg is administered subconjunctivally. In some variations, a total amount of rapamycin less than about 2 mg is administered subconjunctivally. In some variations, a total amount of rapamycin less than about 1.2 mg is administered subconjunctivally. In some variations, a total amount of rapamycin less than about 1.0 mg is administered subconjunctivally. In some variations, a total amount of rapamycin less than about 0.8 mg is administered subconjunctivally. In some variations, a total amount of rapamycin less than about 0.6 mg is administered subconjunctivally. In some variations, a total amount of rapamycin less than about 0.4 mg is administered subconjunctivally. In some variations, a volume of a formulation is administered that contains an amount of rapamycin described herein.

In some variations, a total amount of rapamycin less than about 200 µg is administered intravitreally. In some variations, a total amount of rapamycin less than about 200 µg is administered intravitreally. In some variations, a total amount of rapamycin less than about 300 µg is administered intravitreally. In some variations, a total amount of rapamycin less than about 400 µg is administered intravitreally. In some variations, a total amount of rapamycin less than about 500 µg is administered intravitreally. In some variations, a total amount of rapamycin less than about 600 µg is administered intravitreally. In some variations, a total amount of rapamycin less than about 800 µg is administered intravitreally. In some variations, a total amount of rapamycin less than about 1 mg is administered intravitreally. In some variations, a total amount of rapamycin less than about 2 mg is administered intravitreally. In some variations, a total amount of rapamycin less than about 2.5 mg is administered intravitreally. In some variations, a total amount of rapamycin less than about 3 mg is administered intravitreally. In some variations, a total amount of rapamycin less than about 3.5 mg is administered intravitreally. In some variations, a total amount of rapamycin less than about 4 mg is administered intravitreally. In some variations, a volume of a formulation is administered that contains an amount of rapamycin described herein.

In some variations, a liquid formulation containing a concentration of rapamycin by weight of the total of between about 0.5% and about 6% is subconjunctivally administered to a human subject by administering between about 0.1 µl and about 200 µl of a liquid formulation described herein. In some variations, a liquid formulation containing a concentration of rapamycin by weight of the total of between about 0.5% and about 4% is subconjunctivally administered to a human subject by administering between about 1 µl and about 50 µl of a liquid formulation described herein. In some variations, a liquid formulation containing a concentration of rapamycin by weight of the total of between about 1.5% and about 3.5% is subconjunctivally administered to a human subject by administering between about 1 µl and about 15 µl of a liquid formulation described herein. In some variations, a liquid formulation containing a concentration of rapamycin by weight of the total of about 2% is subconjunctivally administered to a human subject by administering between about 1 µl and about 15 µl of a liquid formulation described herein.

In some variations, a liquid formulation containing an amount of rapamycin of between about 0.2 µg and about 4 µg is subconjunctivally administered to a human subject by administering between about 0.1 µl and about 200 µl of a liquid formulation described herein. In some variations, a liquid formulation containing an amount of rapamycin of between about 20 µg and about 2 mg is subconjunctivally administered to a human subject by administering between about 1 µl and about 100 µl of a liquid formulation described herein. In some variations, a liquid formulation containing an amount of rapamycin of between about 5 µg and about 1 mg is subconjunctivally administered to a human subject by administering between about 1 µl and about 50 µl of a liquid formulation described herein. In some variations, a liquid formulation containing an amount of rapamycin of between about 20 µg and about 500 µg is subconjunctivally administered to a human subject by administering between about 1 µl and about 25 µl of a liquid formulation described herein. In some variations, a liquid formulation containing an: amount of rapamycin of between about 20 µg and about 300 µg is subconjunctivally administered to a human subject by administering between about 1 µl and about 15 µl of a liquid formulation described herein.

In some variations, a total amount of rapamycin less than about 200 µg is administered intravitreally. In some variations, a total amount of rapamycin less than about 200 µg is administered intravitreally. In some variations, a total amount of rapamycin less than about 300 µg is administered intravitreally. In some variations, a total amount of rapamycin less than about 400 µg is administered intravitreally. In some variations, a total amount of rapamycin less than about 500 µg is administered intravitreally. In some variations, a total amount of rapamycin less than about 600 µg is administered intravitreally. In some variations, a total amount of rapamycin less than about 800 µg is administered intravitreally. In some variations, a total amount of rapamycin less than about 1 mg is administered intravitreally. In some variations, a total amount of rapamycin less than about 2 mg is administered intravitreally. In some variations, a total amount of rapamycin less than about 2.5 mg is administered intravitreally. In some variations, a total amount of rapamycin less than about 3 mg is administered intravitreally. In some variations, a total amount of rapamycin less than about 3.5 mg is administered intravitreally. In some variations, a total amount of rapamycin less than about 4 mg is administered intravitreally. In some variations, a volume of a formulation is administered that contains an amount of rapamycin described herein.

In some variations, a liquid formulation containing a concentration of rapamycin by weight of the total of between about 0.5% and about 6% is intravitreally administered to a human subject by administering between about 0.1 µl and about 200 µl of a liquid formulation described herein. In some variations, a liquid formulation containing a concentration of rapamycin by weight of the total of between about 0.5% and about 4% is intravitreally administered to a human subject by administering between about 1 µl and about 50 µl of a liquid formulation described herein. In some variations, a liquid formulation containing a concentration of rapamycin by weight of the total of between about 1.5% and about 3.5% is intravitreally administered to a human subject by administering between about 1 µl and about 15 µl of a liquid formulation described herein. In some variations, a liquid formulation containing a concentration of rapamycin by weight of the total of about 2% is intravitreally administered to a human subject by administering between about 1 µl and about 15 µl of a liquid formulation described herein.

In some variations, a liquid formulation containing an amount of rapamycin of between about 0.2 µg and about 4 mg is intravitreally administered to a human subject by administering between about 0.1 µl and about 200 µl of a liquid formulation described herein. In some variations, a liquid formulation containing an amount of rapamycin of between about 20 µg and about 2 mg is intravitreally administered to a human subject by administering between about 1 µl and about 100 µl of a liquid formulation described herein. In some variations, a liquid formulation containing an amount of rapamycin of between about 20 µg and about 1 mg is intravitreally administered to a human subject by administering between about 1 µl and about 50 µl of a liquid formulation described herein. In some variations, a liquid formulation containing an amount of rapamycin of between about 20 µg and about 500 µg is intravitreally administered to a human subject by administering between about 1 µl and about 25 µl of a liquid formulation described herein. In some variations, a liquid formulation containing an amount of rapamycin of between about 20 µg and about 300 µg is intravitreally administered to a human subject by administering between about 1 µl and about 15 µl of a liquid formulation described herein.

In some variations a formulation as described herein containing an amount of rapamycin of between about 1 µg and about 5 mg is administered to a human subject for treatment of wet AMD. In some variations a formulation as described herein containing an amount of rapamycin of between about 20 µg and about 4 mg is administered to a human subject for treatment of wet AMD. In some variations a liquid formulation as described herein containing an amount of rapamycin of between about 20 µg and about 1.2 mg is administered to a human subject for treatment of wet AMD. In some variations an amount of rapamycin of between about 10 µg and about 0.5 mg is administered to a human subject for treatment of wet AMD. In some variations, an amount of rapamycin of between about 10 µg and 90 µg is administered to a human subject for treatment of wet AMD. In some variations, an amount of rapamycin of between about 60 µg and 120 µg is administered to a human subject for treatment of wet AMD. In some variations, an amount of rapamycin of between about 100 µg and 400 µg is administered to a human subject for treatment of wet AMD. In some variations, an amount of rapamycin of between about 400 µg and 1 mg is administered to a human subject for treatment of wet AMD. In some variations, an amount of rapamycin of between about 1 mg and 5 mg is administered to a human subject for treatment of wet AMD. In some variations, an amount of rapamycin of between about 3 mg and 7 mg is administered to a human subject for treatment of wet AMD. In some variations, an amount of rapamycin of between about 5 mg and 10 mg is administered to a human subject for treatment of wet AMD.

In some variations a formulation as described herein containing an amount of rapamycin of between about 1 µg and about 5 mg is administered to a human subject for prevention of wet AMD. In some variations a formulation as described herein containing an amount of rapamycin of between about 20 µand about 4 mg is administered to a human subject for prevention of wet AMD. In some variations a liquid formulation as described herein containing an amount of rapamycin of between about 20 µg and about 1.2 mg is administered to a human subject for prevention of wet AMD. In some variations an amount of rapamycin of between about 10 µg and about 0.5 mg is administered to a human subject for prevention of wet AMD. In some variations, an amount of rapamycin of between about 10 µg and 90 µg is administered to a human subject for prevention of wet AMD. In some variations, an amount of rapamycin of between about 60 µg and 120 µg is administered to a human subject for prevention of wet AMD. In some variations, an amount of rapamycin of between about 100 µg and 400 µg is administered to a human subject for prevention of wet AMD. In some variations, an amount of rapamycin of between about 400 µg and 1 mg is administered to a human subject for prevention of wet AMD. In some variations, an amount of rapamycin of between about 1 mg and 5 mg is administered to a human subject for prevention of wet AMD. In some variations, an amount of rapamycin of between about 3 mg and 7 mg is administered to a human subject for prevention of wet AMD. In some variations, an amount of rapamycin of between about 5 mg and 10 mg is administered to a human subject for prevention of wet AMD. In some variations, prevention of wet AMD is prevention of the transition from dry AMD to wet AMD.

In some variations a formulation as described herein containing an amount of rapamycin of between about 1 µg and about 5 mg is administered to a human subject for treatment of dry AMD. In some variations a formulation as described herein containing an amount of rapamycin of between about 20 µg and about 4 mg is administered to a human subject for treatment of dry AMD. In some variations a liquid formulation as described herein containing an amount of rapamycin of between about 20 µg and about 1.2 mg is administered to a human subject for treatment of dry AMD. In some variations an amount of rapamycin of between about 10 µg and about 0.5 mg is administered to a human subject for treatment of dry AMD. In some variations, an amount of rapamycin of between about 10 µg and 90 µg is administered to a human subject for treatment of dry AMD. In some variations, an amount of rapamycin of between about 60 µg and 120 µg is administered to a human subject for treatment of dry AMD. In some variations, an amount of rapamycin of between about 100 µg and 400 µg is administered to a human subject for treatment of dry AMD. In some variations, an amount of rapamycin of between about 400 µg and 1 mg is administered to a human subject for treatment of dry AMD. In some variations, an amount of rapamycin of between about 1 mg and 5 mg is administered to a human subject for treatment of dry AMD. In some variations, an amount of rapamycin of between about 3 mg and 7 mg is administered to a human subject for treatment of dry AMD. In some variations, an amount of rapamycin of between about 5 mg and 10 mg is administered to a human subject for treatment of dry AMD.

In some variations, a liquid formulation as described herein containing an amount of rapamycin of between about 1 µg and about 5 mg is administered to a human subject for treatment of angiogenesis, including but not limited to choroidal neovascularization. In some variations for treatment of angiogenesis, including but not limited to choroidal neovascularization, a formulation as described herein containing an amount of rapamycin of between about 1 µg and about 5 mg is administered to a human subject. In some variations for treatment of angiogenesis, including but not limited to choroidal neovascularization, a formulation as described herein containing an amount of rapamycin of between about 20 µg and about 4 mg, between about 20 µg and about 1.2 mg, between about 10 µg and about 0.5 mg, between about 10 µg and 90 µg between about 60 µg and 120 µg, between about 100 µg and 400 µg, between about 400 µg and 1 mg, or between about 1 mg and 5 mg is administered to the human subject.

In some variations, any one or more of the rapamycin formulations described herein are administered intravitreally every 3 or more months, every 6 or more months, every 9 or more months, or every 12 or more months, or longer, to treat one or more of choroidal neovascularization, wet AMD, dry AMD, to prevent wet AMD, or to prevent progression of dry AMD to wet AMD. In some variations, any one or more of the rapamycin formulations described herein are administered subconjunctivally every 3 or more months, every 6 or more months, every 9 or more months, or every 12 or more months, or longer, to treat one or more of choroidal neovascularization, wet AMD, dry AMD, to prevent wet AMD, or to prevent progression of dry AMD to wet AMD. In some variations, the effect of the rapamycin persists beyond the period during which it is present in the ocular tissues.

In some variations, any one or more of the formulations described herein are administered intravitreally every 3 or more months, every 6 or more months, every 9 or more months, or every 12 or more months, or longer, to prevent one or more of choroidal neovascularization, wet AMD, dry AMD, or to prevent wet AMD. In some variations, any one or more of the formulations described herein are administered subconjunctivally every 3 or more months, every 6 or more months, every 9 or more months, or every 12 or more months, or longer, to prevent one or more of choroidal neovascularization, wet AMD, dry AMD, or to prevent wet AMD.

Rapamycin may, for example, be delivered at a dosage range between about 1 ng/day and about 100 µg/day, or at dosages higher or lower than this range, depending on the route and duration of administration. In some variations of liquid formulation or composition used in the methods described herein, rapamycin is delivered at a dosage range of between about 0.1 µg/day and about 10 µg/day. In some variations of liquid formulation or composition used in the methods described herein, rapamycin is delivered at a dosage range of between about 1 µg/day and about 5 µg/day. Dosages of rapamycin for treatment, prevention, inhibition, delay of onset, or cause of regression of various diseases and conditions described herein can be refined by the use of clinical trials.

The liquid formulations and compositions described herein may be used for delivery to the eye, as one nonlimiting example by ocular or periocular administration, of therapeutically effective amounts of rapamycin for extended periods of time to treat, prevent, inhibit, delay the onset of, or cause regression of CNV, and thus may be used to treat, prevent, inhibit, delay the onset of, or cause regression of wet AMD. It is believed that by changing certain characteristics of the liquid formulations and compositions described herein, including but not limited to the volume, positioning and components of the liquid formulations, the liquid formulations and compositions described herein may be used to deliver therapeutically effective amounts of rapamycin to the eye for a variety of extended time periods including delivery of therapeutic amounts for greater than about 1 week, for greater than about 2 weeks, for greater than about 3 weeks, for greater than about 1 month, for greater than about 3 months, for greater than about 6 months, for greater than about 9 months, for greater than about 1 year.

When a therapeutically effective amount of rapamycin is administered to a subject suffering from wet AMD, the rapamycin may treat, inhibit, or cause regression of the wet AMD. Different therapeutically effective amounts may be required for treatment, inhibition or causing regression. A subject suffering from wet AMD may have CNV lesions, and it is believed that administration of a therapeutically effective amount of rapamycin may have a variety of effects, including but not limited to causing regression of the CNV lesions, stabilizing the CNV lesion, and preventing progression of an active CNV lesion.

When a therapeutically effective amount of rapamycin is administered to a subject suffering from dry AMD, it is believed that the rapamycin may prevent or slow the progression of the dry AMD.

In some variations, a liquid rapamycin formulation described herein is administered in combination with other therapeutic agents and therapies, including but not limited to agents and therapies useful for the treatment, prevention, inhibition, delaying onset of, or causing regression of angiogenesis or neovascularization, particularly CNV. In some variations the additional agent or therapy is used to treat regression of angiogenesis or neovascularization, particularly CNV. Non-limiting examples of such additional agents and therapies include pyrrolidine, dithiocarbamate (NFκB inhibitor); squalamine; TPN 470 analogue and fumagillin; PKC (protein kinase C) inhibitors; Tie-1 and Tie-2 kinase inhibitors; inhibitors of VEGF receptor kinase; proteosome inhibitors such as Velcade™ (bortezomib, for injection; ranibuzumab (Lucentis™) and other antibodies directed to the same target; pegaptanib (Macugen™); vitronectin receptor antagonists, such as cyclic peptide antagonists of vitronectin receptor-type integrins; α-v/β-3 integrin antagonists; α-κ/β-1 integrin antagonists; thiazolidinediones such as rosiglitazone or troglitazone; interferon, including γ-interferon or interferon targeted to CNV by use of dextran and metal coordination; pigment epithelium derived factor (PEDF); endostatin; angiostatin; tumistatin; canstatin; anecortave acetate; acetonide; triamcinolone; tetrathiomolybdate; RNA silencing or RNA interference (RNAi) of angiogenic factors, including ribozymes that target VEGF expression; Accutane™ (13-cis retinoic acid); ACE inhibitors, including but not limited to quinopril, captopril, and perindozril; inhibitors of mTOR (mammalian target of rapamycin); 3-aminothalidomide; pentoxifylline; 2-methoxyestradiol; colchicines; AMG-1470; cyclooxygenase inhibitors such as nepafenac, rofecoxib, diclofenac, rofecoxib, NS398, celecoxib, vioxx, and (E)-2-alkyl-2(4-methanesulfonylphenyl)-1-phenylethene; t-RNA synthase modulator; metalloprotease 13 inhibitor; acetylcholinesterase inhibitor; potassium channel blockers; endorepellin; purine analog of 6-thioguanine; cyclic peroxide ANO-2; (recombinant) arginine deiminase; epigallocatechin-3-gallate; cerivastatin; analogues of suramin; VEGF trap molecules; inhibitors of hepatocyte growth factor (antibodies to the growth factor or its receptors, small molecular inhibitors of the c-met tyrosine kinase, truncated versions of HGF e.g. NK4); apoptosis inhibiting agents; Visudyne™, snET2 and other photo sensitizers with photodynamic therapy (PDT); and laser photocoagulation.

EXAMPLES

Unless the context indicates otherwise, the error bars in the charts show one standard deviation. Where ethanol is used, it is 200 proof ethanol from Gold Shield Distributors, Hayward, Calif. Where rapamycin is used, it is from LC laboratories, Woburn, Mass., or Chunghwa Chemical Synthesis & Biotech Co., LTD (CCSB), Taipei Hsien, Taiwan, ROC. Where PEG 400 is used, it is from The Dow Chemical Company, New Milford, Conn. As used herein, "% w/w" means the weight of the component divided by the total formulation weight. Some of the graphs use the expression "uL" or "ug" to refer to µL or µg, respectively.

Example 1

Preparation and Characterization of a Rapamycin-Containing Solution

About 320 g of ethanol was sparged with $N_2$ for about 10 minutes, and then about 40 g of sirolimus was added to the ethanol. The mixture was sonicated for about 20 minutes, by the end of which all of the sirolimus had gone into solution to form a sirolimus stock solution. A diluent non-aqueous liquid component was prepared by sonicating about 1880 g of PEG 400 for about 60 minutes, and then sparging the non-aqueous liquid component with nitrogen for about 10 minutes.

The sirolimus stock solution and the PEG 400 were then rotated at about room temperature in a rotary evaporator for about 10 minutes to mix the stock solution with the diluent non-aqueous liquid component. After mixing, the solution was sparged with nitrogen for about 10 minutes and blanketed with nitrogen for about 5 minutes. After the solution was sparged and filled with nitrogen, about 240 g of excess ethanol was evaporated from the solution by increasing the solution temperature, maintaining a temperature that did not exceed 40° C. for an extended period of time and continuing to rotate the solution for about 2.5 hours.

The resulting solution comprised about 40 g of sirolimus (about 2% w/w), about 80 g of ethanol (about 4% w/w), and about 1880 g of PEG 400 (about 94% w/w). This solution was sparged with nitrogen for about 10 minutes and blanketed with nitrogen for about 5 minutes. The solution was then filtered through a 0.2 micron filter. HPLC vials were filled with 2 ml each of the filtered solution to leave a head space in each container of about 400 µl. This head space was filled with nitrogen gas and capped.

Example 2

Preparation and Characterization of a Rapamycin-Containing Solution

Rapamycin, ethanol and PEG 400 were placed in a container to give final concentrations by weight of about 2.00% w/w rapamycin, about 4.00% w/w ethanol, and about 94.00% w/w PEG 400. The mixture was capped and sonicated for 1-2 hours. The sonication generated heat, with temperatures of up to about 40 or 50° C. Volumes of 1 µl, 3 µl, 20 µl, and 40 µl formed a non-dispersed mass in the vitreous of rabbit eyes.

Example 3

Subconjunctival Injection of a Rapamycin-Containing Solution

Figure 3:
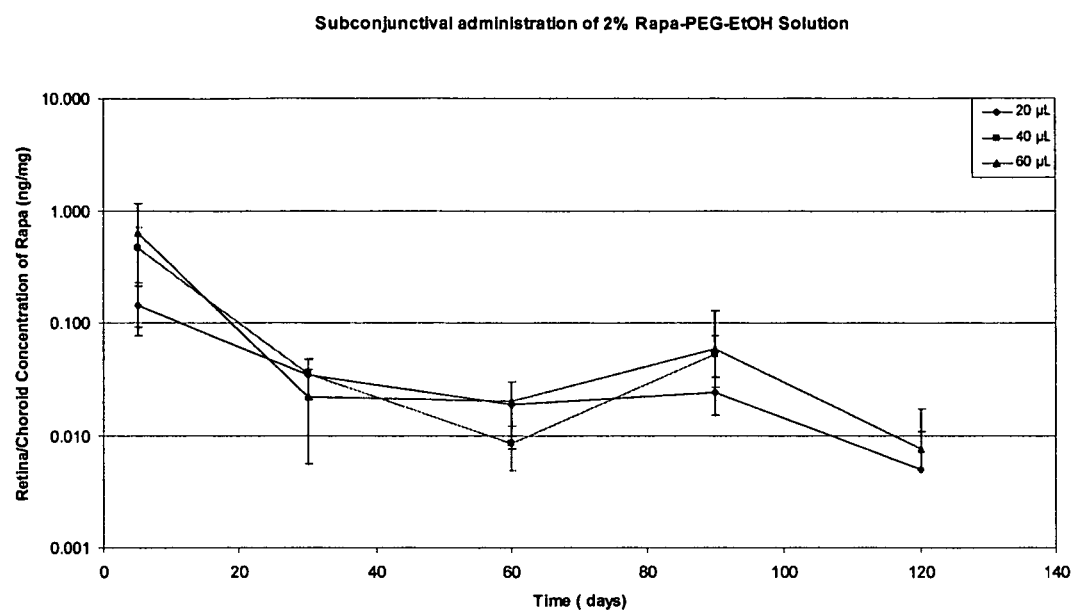
FIG. 3 depicts the level of rapamycin in the retina choroid tissues of rabbit eyes (ng/mg) at 5, 30, 60, 90, and 120 days after subconjunctival injection of 20 µl, 40 µl, and 60 µl doses of a 2% solution of rapamycin in ethanol and PEG 400.

20 µl of the solution described in Example 2 were injected between the sclera and the conjunctiva of the eye of New Zealand white rabbits. FIG. 2 depicts the level of rapamycin in the vitreous on a logarithmic scale at 5, 30, 60, 90, and 120 days after injection. FIG. 3 depicts the level of rapamycin in the retina choroid on a logarithmic scale at the same time points. For comparison, FIG. 2 and FIG. 3 also depict results of similar studies, performed with 40 µl and 60 µl injections, described below in Example 4 and Example 5.

In FIGS. 2-5, discussed in this and following examples, some outlier points have been omitted. Individual data points from the same study at the same time point were compared to each other. When the arithmetic mean of the data points was lower than their standard deviation, the data points that were higher or lower by an order of magnitude were considered as outliers.

The analysis was by liquid chromatography mass spectroscopy (LCMS) using an internal standard.

At each timepoint, the average concentration of rapamycin was calculated by adding the concentrations of rapamycin obtained for each eye from each rabbit, and dividing the total by the number of eyes analyzed.

The full vitreous was homogenized and analyzed. The average concentration of the vitreous was calculated by dividing the mass of rapamycin measured by the volume of vitreous analyzed. Where injection is intravitreal, for samples other than the vitreous, the sample did not include the site of administration; thus, this measurement indicated the level of rapamycin delivered to the vitreous via the solution. Where injection was intravitreal, for vitreous samples, the sample is thought to include the site of administration; thus, this measurement indicated the level of rapamycin cleared from the vitreous.

The full retina choroid was homogenized and analyzed. The average concentration of the retina choroid was calculated by dividing the mass of rapamycin measured by the mass of retina choroid analyzed.

Where injection was intravitreal or subconjunctival, the sample did not include the site of administration; thus, this measurement indicated the level of rapamycin delivered to the retina choroid via the solution.

In this experiment, between two and five rabbit eyes were analyzed at each time point. The vitreous sample did not include the site of administration, so this measurement indicated the level of rapamycin delivered to the vitreous. The average level of rapamycin in the vitreous at 5, 30, 60, 90, and 120 days after subconjunctival injection was about 1.81, 0.45, 0.39, 1.85, and 1.49 ng/ml, respectively.

The retina choroid was homogenized and analyzed as described in Example 3, with the samples taken as described for the vitreous above. The retina choroid did not include the site of administration, so this measurement indicated the level of rapamycin delivered to the retina choroid. The average level of rapamycin in the retina choroid at 5, 30, 60, 90, and 120 days after subconjunctival injection was about 0.14, 0.03, 0.02, 0.02, and 0.01 ng/mg, respectively.

Example 4

Subconjunctival Injection of a Rapamycin-Containing Solution

40 µl of the solution described in Example 2 were injected between the sclera and the conjunctiva of the eye of New Zealand white rabbits. FIG. 2 depicts the level of rapamycin in the vitreous on a logarithmic scale at 5, 30, 60, 90, and 120 days after injection. FIG. 3 depicts the level of rapamycin in the retina choroid on a logarithmic scale at the same time points.

The vitreous was homogenized and analyzed as described in Example 3. Between two and five rabbit eyes were analyzed at each time point. The vitreous sample did not include the site of administration, so this measurement indicated the level of rapamycin delivered to the vitreous. The average level of rapamycin in the vitreous at 5, 30, 60, 90, and 120 days after subconjunctival injection was about 2.39, 0.65, 0.54, 2.07, and 1.92 ng/ml, respectively.

The retina choroid was homogenized and analyzed as described in Example 3, with the samples taken as described for the vitreous above. The retina choroid did not include the site of administration, so this measurement indicated the level of rapamycin delivered to the retina choroid. The average level of rapamycin in the retina choroid at 5, 30, 60, 90, and 120 days after subconjunctival injection was about 0.47, 0.04, 0.01, 0.05, and 0.0 ng/mg, respectively.

Example 5

Subconjunctival Injection of a Rapamycin-Containing Solution

60 µl of the solution described in Example 23 were injected between the sclera and the conjunctiva of the eye of New Zealand white rabbits. FIG. 2 depicts the level of rapamycin in the vitreous on a logarithmic scale at 5, 30, 60, 90, and 120 days after injection. FIG. 3 depicts the level of rapamycin in the retina choroid on a logarithmic scale at the same time points.

vitreous was homogenized and analyzed as described in Example 3. Between two and five rabbit eyes were analyzed at each time point. The vitreous sample did not include the site of administration, so this measurement indicated the level of rapamycin delivered to the vitreous. The average level of rapamycin in the vitreous at 5, 30, 60, 90, and 120 days after subconjunctival injection was about 8.65, 0.29, 0.18, 2.00, 1.41 ng/ml, respectively.

The retina choroid was homogenized and analyzed as described in Example 3, with the samples taken as described for the vitreous above. The retina choroid did not include the site of administration, so this measurement indicated the level of rapamycin delivered to the retina choroid. The average level of rapamycin in the retina choroid at 5, 30, 60, 90, and 120 days after subconjunctival injection was about 0.63, 0.02, 0.02, 0.06, and 0.01 ng/mg, respectively.

Example 6

Intravitreal Injection of a Rapamycin-Containing Solution

Figure 4:
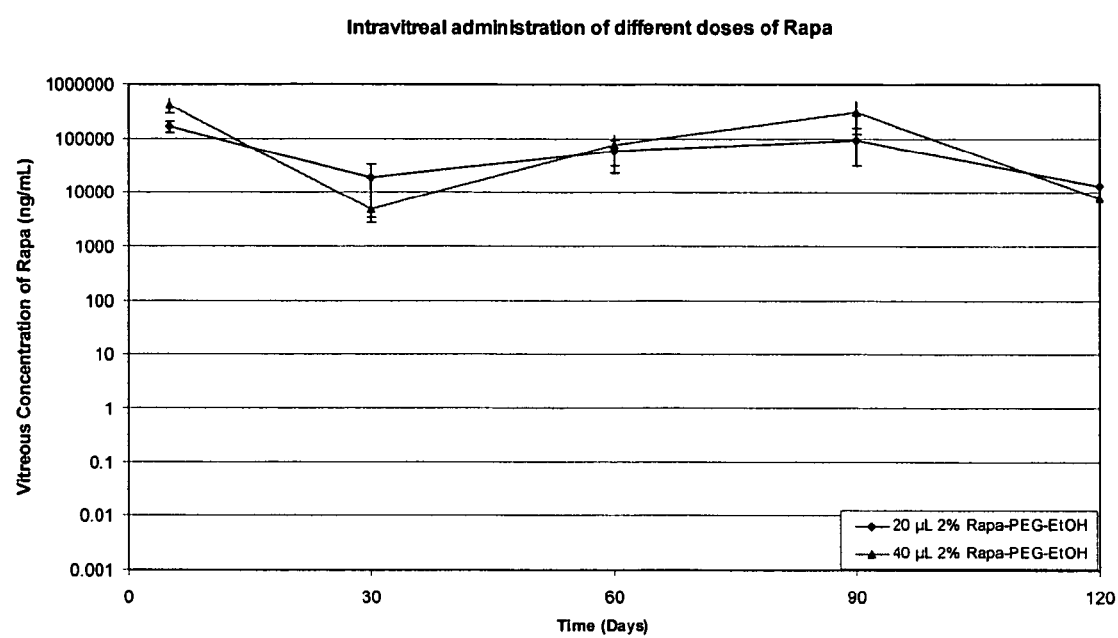
FIG. 4 depicts the level of rapamycin in the vitreous of rabbit eyes (ng/ml) at 5, 30, 60, 90, and 120 days after intravitreal injection of 20 µl and 40 µl doses of a 2% solution of rapamycin in ethanol and PEG 400.
Figure 5:
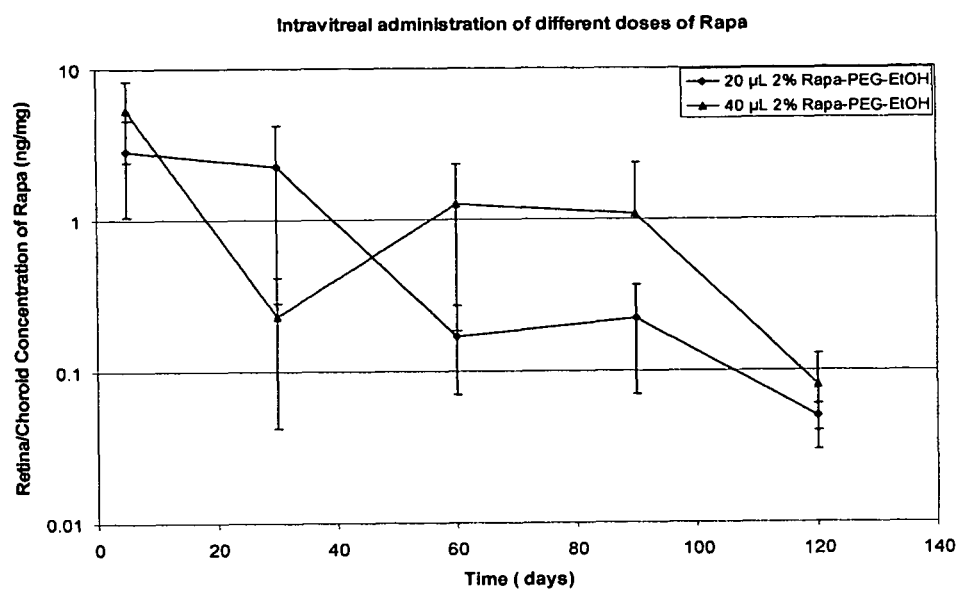
FIG. 5 depicts the level of rapamycin in the retina choroid tissues of rabbit eyes (ng/mg) at 5, 30, 60, 90, and 120 days after intravitreal injection of 20 µl and 40 µl doses of a 2% solution of rapamycin in ethanol and PEG 400.

20 μl of the solution described in Example 2 were injected into the vitreous of the eye of New Zealand white rabbits. The injected solution formed a non-dispersed mass relative to the surrounding medium. FIG. 4 depicts the level of rapamycin in the vitreous on a logarithmic scale 5, 30, 60, 90, and 120 days after injection. FIG. 5 depicts the level of rapamycin in the retina choroid on a logarithmic scale at the same time points. For comparison, FIG. 4 and FIG. 5 also depict results of other studies described below in Example 28 and Example 30.

The vitreous was homogenized and analyzed as described in Example 3. Between two and five rabbit eyes were analyzed at each time point. The vitreous sample may have included the site of administration. The average level of rapamycin in the vitreous at 5, 30, 60, 90, and 120 days after intravitreal injection was about 162,100; 18,780; 57,830; 94,040; and 13,150 ng/ml, respectively.

The retina choroid was homogenized and analyzed as described in Example 3, with the samples taken as described for the vitreous above. The retina choroid did not include the site of administration, so this measurement indicated the level of rapamycin delivered to the retina choroid. The average level of rapamycin in the retina choroid at 5, 30, 60, 90, and 120 days after intravitreal injection was about 2.84, 2.26, 0.17, 0.22, and 0.05 ng/mg, respectively.

Example 7

Intravitreal Injection of a Rapamycin-Containing Solution

40 μl of the solution described in Example 2 were injected into the vitreous of the eye of New Zealand white rabbits. The injected solution formed a non-dispersed mass relative to the surrounding medium. FIG. 4 depicts the level of rapamycin in the vitreous on a logarithmic scale 5, 30, 60, 90, and 120 days after injection. FIG. 5 depicts the level of rapamycin in the retina choroid on a logarithmic scale at the same time points.

The vitreous was homogenized and analyzed as described in Example 3. Between two and five rabbit eyes were analyzed at each time point. The vitreous sample may have included the site of administration. The average level of rapamycin in the vitreous at 5, 30, 60, 90, and 120 days after intravitreal injection was about 415,600; 4,830; 74,510; 301,300; and 7,854 ng/ml respectively.

The retina choroid was homogenized and analyzed as described in Example 3, with the samples taken as described for the vitreous above. The retina choroid did not include the site of administration, so this measurement indicated the level of rapamycin delivered to the retina choroid. The average level of rapamycin in the retina choroid at 5, 30, 60, 90, and 120 days after intravitreal injection was about 5.36, 0.23, 1.27, 1.08, and 0.08 ng/mg, respectively.

All references cited herein, including patents, patent applications, and publications, are hereby incorporated by reference in their entireties, whether previously specifically incorporated or not.

What is claimed is:

1. A method for treating wet age-related macular degeneration in a human subject, the method comprising administering to the human subject by intraocular or periocular injection of a liquid formulation containing an amount of rapamycin effective to treat wet-age macular degeneration in the human subject, wherein the liquid formulation is a liquid solution that forms a non-dispersed mass when injected into the vitreous, and the liquid formulation comprises about 2% (w/w) rapamycin, about 94% (w/w) PEG 400, and about 4% (w/w) ethanol.

2. The method of claim 1, wherein the volume of liquid formulation contains between 20 μg and 2.5 mg of rapamycin.

3. The method of claim 1, wherein the volume of liquid formulation contains between 20 μg and 4 mg of rapamycin.

4. The method of claim 1, wherein the volume of the liquid formulation is administered to the human subject by injection into the vitreous.

5. The method of claim 1, wherein the volume of the liquid formulation is administered to the human subject by injection between the sclera and conjunctiva.

6. The method of claim 1, wherein the volume of the liquid formulation when injected into the vitreous delivers an amount of rapamycin sufficient to achieve one or both of:
   an average concentration of rapamycin in the retina choroid of at least 0.01 ng/mg for a period of time of at least 30 days following administration of the liquid formulation, and
   an average concentration of rapamycin in the vitreous of at least 1000 ng/ml for a period of time of at least 30 days following administration of the liquid formulation.

7. The method of claim 1, wherein the volume of the liquid formulation when injected between the sclera and conjunctiva delivers an amount of rapamycin sufficient to achieve one or both of:
   an average concentration of rapamycin in the vitreous of at least 0.01 ng/ml for a period of time of at least 30 days following administration of the liquid formulation; and
   an average concentration of rapamycin in the retina choroid of at least 0.001 ng/mg for a period of time of at least 30 days following administration of the liquid formulation.

8. The method of claim 1, wherein the non-dispersed mass is a solid depot of rapamycin.

* * * * *

UNITED STATES PATENT AND TRADEMARK OFFICE
CERTIFICATE OF CORRECTION

| | | |
|---|---|---|
| PATENT NO. | : 8,637,070 B2 | Page 1 of 1 |
| APPLICATION NO. | : 11/352092 | |
| DATED | : January 28, 2014 | |
| INVENTOR(S) | : Mudumba et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1385 days.

Signed and Sealed this
Second Day of June, 2015

Michelle K. Lee
*Director of the United States Patent and Trademark Office*